(12) United States Patent
O'Malley et al.

(10) Patent No.: US 6,416,998 B1
(45) Date of Patent: *Jul. 9, 2002

(54) PLASMID ENCODING A MODIFIED STEROID HORMONE

(75) Inventors: Bert W. O'Malley; Ming-Jer Tsai, both of Houston; Harry C. Ledebur, Jr., Spring; Joseph D. Kittle, Jr., Houston, all of TX (US)

(73) Assignees: Baylor College of Medicine, Houston; Valentis, Inc., The Woodlands, both of TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/479,913

(22) Filed: Jun. 7, 1995

Related U.S. Application Data

(63) Continuation-in-part of application No. 07/939,246, filed on Sep. 2, 1992, now abandoned.

(51) Int. Cl.⁷ .................... C12N 15/12; C12N 15/62; C12N 15/85

(52) U.S. Cl. .............. 435/325; 536/23.5; 536/23.4; 435/252.3; 435/320.1

(58) Field of Search ................... 435/69.1, 69.7, 435/240.1, 320.1, 252.3, 325; 536/23.5, 23.4

(56) References Cited

U.S. PATENT DOCUMENTS

| | | | |
|---|---|---|---|
| 4,736,866 A | 4/1988 | Leder et al. ............ 800/1 |
| 4,981,784 A | * 1/1991 | Evans et al. ............ 435/6 |
| 5,283,173 A | 2/1994 | Fields et al. ............ 435/6 |
| 5,298,422 A | 3/1994 | Schwartz et al. ........ 435/320.1 |
| 5,364,791 A | 11/1994 | Vegeto et al. ............ 435/320.1 |

FOREIGN PATENT DOCUMENTS

| | | |
|---|---|---|
| EP | 0 371 820 A | 6/1990 |
| WO | 9007517 | 7/1990 |
| WO | 9014356 | 11/1990 |
| WO | 92/22567 A | 12/1992 |
| WO | 9318759 | 9/1993 |
| WO | 9323431 | 11/1993 |
| WO | 96/40911 | 12/1996 |

OTHER PUBLICATIONS

Hollenberg et al. Cell 49 (1987) 39–46.*
Rudinger "Peptide Hormones", ed. J.A. Parsons, ©1976, pp. 1–7.*
Kellendonk, et al., "Regulation of Cre Recombinase Activity by the Synthetic Steroid RU 486," *Nucleic Acids Research* 24(8):1404–1411 (1996).
Lanz, et al., "Active, Interactive, and Inactive Steroid Receptors Mutants," *Steroids* 59:148–152 (1994).
Laudet, "Les Recepteurs Nucleaires," *Pour La Science* 183:32–39 (1993).
Lewin, "Genes V," Oxford University Press, Oxford (1994), pp. 889–897.
Malchoff, et al., "A Mutation of the Glucocorticoid Receptor in Primary Cortisol Resistance," *Journal of Clinical Investigation* 91(5):1918–1925 (1993).
Veldscholte, et al., "Anti–Androgens and the Mutated Androgen Receptor of LNCaP Cells: Differential Effects on Binding Affinity, Heat–Shock Protein Interaction, and Transription Activation," *Biochemistry* 31:2393–2399 (1992).
Wurtz, et al., "A Canonical Structure for the Ligand–Binding Domain of Nuclear Receptors," *Natural Structural Biology* 3:87–94 (1996).
Strasser–Wozak et al., "Splice Site Mutation in the Glucocorticoid Receptor Gene Causes Resistance to Glucocorticoid–induced Apoptosis in a Human Acute Leukemic Cell Line," *Cancer Research* 55:348–353 (1995).
Chen and Stallcup, "The Hormone–binding Role of 2 Cysteines Near the C Terminus of The Mouse Glucocorticoid Receptor," *J. Biol. Chem.* 269:7914–7918 (1994).
Byravan et al., "Two point mutations in the hormone–binding domain of the mouse glucocorticoid receptor that dramatically reduce its function," *Chemical Abstracts* 115:104 at abstract No. 85664 (1991).
Burnstein et al., "Intragenic sequences of the human glucocorticoid receptor complementary DNA mediate hormone–inducible receptor messenger RNA down–regulation through multiple mechanisms," *Chemical Abstracts* 122:152 at abstract No. 46745 (1994).
Muller et al., "Multiple domains of the glucocorticoid receptor involved in synergism with the CACCC box factor(s)," *Chemical Abstracts* 115:127 at abstract No. 270937 (1991).
Akerblom et al., "Negative Regulation by Glucocorticoids Through Interference with a cAMP Responsive Enhancer," *Science* 241:350–353 (1988).
Allan et al., "Hormone and Antihormone Induce Distinct Conformational Changes Which are Central to Steroid Receptor Activation," *J. Biol. Chem.* 267:19513–19520 (1992).
Allan et al., "Ligand–dependent conformational changes in the progesterone receptor are necessary for events that follow DNA binding," *Proc. Natl. Acad. Sci. USA* 89:11750–11754 (1992).
Barzel, U., "Estrogens in the Prevention and Treatment of Postmenopausal Osteoporosis: A review," *Am. J. Med.* 85:847–850 (1988).
Beato, M., "Gene Regulation by Steroid Hormones," *Cell* 56:335–344 (1989).

(List continued on next page.)

Primary Examiner—Gary L. Kunz
Assistant Examiner—Robert C. Hayes
(74) Attorney, Agent, or Firm—Lyon & Lyon LLP

(57) ABSTRACT

The present invention provides mutated proteins of steroid hormone receptors. These mutated proteins are useful as gene medicines. In particular, these mutated proteins are useful for regulating expression of genes in gene therapy. In addition, the present invention provides plasmids encoding for the desired mutated steroid hormone receptor proteins, as well as cells transfected with those plasmids.

2 Claims, 13 Drawing Sheets

OTHER PUBLICATIONS

Beato, M. "Transcriptional control by nuclear receptors," *FASEB J.* 5:2044–2051 (1991).

Beekman et al., "Transcriptional Activation by the Estrogen Receptor Requires a Conformational Change in the Ligand Binding Domain," *Mol. Endocrinol.* 7:1266–1274 (1993).

Berry et al., *EMBO J.* 9(9):2811–2818 (1990).

Cato et al., "Steroids and Growth Promoting Factors in the Regulation of Expression of Genes and Gene Networks," *J. Steroid Biochem. Molec. Biol.* 43:63–68 (1992).

Celada et al., "Repression of Major Histocompatibility Complex IA Expression by Glucorticoids: The Glucocorticoid Receptor Inhibits the DNA Binding of the X Box DNA Binding Protein," *J. Exp. Med.* 177:691–698 (1993).

Chu et al., "Efficiency of Cytoplasmic Delivery by ph–Sensitive Liposomes to the Cells in Culture," *Pharmaceutical Research* 7:824–834 (1990).

Dahlman–Wright et al., "Interaction of the Glucocorticoid Receptor DNA–binding Domain with DNA as a Dimer Is Mediated by a Short Segment of Five Amino Acids," *J. Biol. Chem.* 266:3107–3112 (1991).

Daneshgari et al., "Endocrine Therapy of Advanced Carcinoma of the Prostate," *Cancer* 71:1089–1097 (1993).

Denis et al., "Requirement of hormone for thermal conversion of the glucocorticoid receptor to a DNA–binding state," *Nature* 333:686–688 (1988).

Denis et al., "The Molybdate–stabilized Nonactivated Glucocorticoid Receptor Contains a Dimer of $M_2$ 90,000 Non–hormone–binding Protein," *J. Biol. Chem.* 262:11803–11806 (1987).

Diamond et al., "Transcriptional Factor Interactions: Selectors of Positive or Negative Regulation from a Single DNA Element," *Science* 249:1266–1272 (1990).

Dobson et al., "Mutational Analysis of the Chicken Progesterone Receptor," *J. Biol. Chem.* 264:4207–4211 (1989).

Dreicer and Wilding, "Steroid Hormone Agonists and Antagonists in the Treatment of Cancer," *Cancer Investigation* 10:27–41 (1992).

Drouin et al., "Glucocorticoid Receptor Binding to a Specific DNA Sequence is Required for Hormone–Dependent Repression of Pro–Opiomelanocortin Gene Transcription," *Molecular and Cellular Biology* 9:5305–5314 (1989).

Evans, "The Steroid and Tyroid Hormone Receptor Superfamily," *Science* 240:889–895 (1988).

Fuller et al., "The steroid receptor superfamily: mechanisms of diversity," *FASEB J.* 5:3092–3099 (1991).

Gauthier et al., "Functional interference between the Spi–1/Pu.1 oncoprotein and steroid hormone or vitamin receptors," *EMBO J.* 12:5089–5096 (1993).

Haensler and Szoka, "Synthesis and Characterization of a Trigalactosylated Bisacridine Compound to Target DNA to Hepatocytes," *Bioconjugate Chem.* 4:85–93 (1993).

Heck et al., "A distinct modulating domain in glucocorticoid receptor monomers in the repression of activity of the transcription factor AP–1," *EMBO J.* 13:4087–4095 (1994).

Hollenberg and Evans, "Multiple and Cooperative Trans–Activation Domains of the Human Glucocorticoid Receptor," *Cell* 55:899–906 (1986).

Howard and Distelhorst, "Evidence for Intracellular Association of the Glucocorticoid Receptor with the 90–kDa Heat Shock Protein," *J. Biol. Chem.* 263:3474–3481 (1988).

Ito et al., "Transformation of Intact Yeast Cells Treated with Alkali Cations," *J. Bacteriol.* 153:163–168 (1983).

Jonat et al., "Antitumor Promotion and Antiinflammation: Down–Modulation of AP–1 (Fos/Jun) Activity by Glucocorticoid Hormone," *Cell* 62:1189–1204 (1990).

Kawai et al., "New Procedure for DNA Transfection with Polycation and Dimethyl Sulfoxide," *Mol. Cell. Biol.* 4:1172–1174 (1984).

Kerppola et al., "Fos is a Preferential Target of Glucocorticoid Receptor Inhibition of AP–1 Activity In Vitro," *Moll. Cell. Biol.* 13:3782–3791 (1993).

Kutoh et al., "Functional Inteference between the Ubiquitous and Constitutive Octamer Transcription Factor 1 (OTF–1) and the Glucocorticoid Receptor by Direct Protein–Protein Interaction Involving the Homeo Subdomain of OTF–1," *Mol. Cell. Biol.* 12:4960–4969 (1992).

Lanz and Rusconi, "A Conserved Carboxy–Terminal Subdomain Is Important for Ligand Interpretation and Transactivation by Nuclear Receptors," *Endocrinology* 135:2183–2195 (1994).

Lebeau et al., "P59, an hsp 90–binding Protein," *J. Biol. Chem.* 267:4281–4284 (1992).

Legendre and Szoka, "Cyclic amphipathic peptide—DNA complexes mediate high–efficency transfection of adherent mammalian cells," *Proc. Natl. Acad. Sci. USA* 90:893–897 (1993).

Legendre and Szoka, "Delivery of Plasmid DNA into Mammalian Cell Lines Using pH–Sensitive Liposomes: Comparison with Cationic Liposomes," *Pharmaceutical Research* 9:1235–1242 (1992).

Lerner et al., "Isolation of Subtilisin Pro–sequence Mutations that Affect Formation of Active Protease by Localized Random Polymerase Chain Reaction Mutagenesis," *J. Biol. Chem.* 265:20085–20086 (1990).

Liu et al., "Hormone–Independent Repression of AP–1–Inducible Collagenase Promoter Activity by Glucocorticoid Receptors," *Mol. Cell. Biol.* 15:1005–1013 (1995).

Lucibello et al., "Mutual transrepression of Fos and the glucocorticoid receptor: involvement of a functional domain in Fos which is absent in FosB," *EMBO J.* 9:2827–2843 (1990).

Mak et al., "Expression of Functional Chicken Oviduct Progesterone Receptors in Yeast (*Saccharomyces cerevisiae*)," *J. Biol. Chem.* 264:21613–21618 (1989).

McDonnell et al., "Reconstitution of the vitamin D–Responsive Osteocalcin Transcription Unit in *Saccharomyces cerevisiae*," *Mol. Cell. Biol.* 9:3517–3523 (1989).

Mendel et al., "Molybdate–stabilized Nonactivated Glucocorticoid–Receptor Complexes Contain a 90–kDa Non–steroid–binding Phosphoprotein That is Lost on Activation," *J. Biol. Chem.* 261:3758–3763 (1986).

Meyer et al., *EMBO J.* 9:3923–3932 (1990).

Miller, "Assay of β–Galactosidase," *Experiments in Molecular Genetics,* CSHL pp. 352–355 (1972).

Miner et al., "Joints in the Regulatory Lattice: Composite Regulation by Steroid Receptor–AP1 Complexes," *Cell Growth & Differ.* 2:525–530 (1991).

Misrahi et al., "Complete Amino Acid Sequence of the Human Progesterone Receptor Deduced from Cloned cDNA," *Biochem. Biophys. Res. Commun.* 143:740–749 (1987).

Mordacq and Linzer, "Co–localization of elements required for phorbol ester stimulation and glucocorticoid repression of proliferin gene expression," *Genes & Development* 3:760–769 (1989).

O'Malley and Tsai, "Molecular Pathways of Steroid Receptor Action," *Biol. Reprod.* 46:163–167 (1992).

Oro et al., "Transcriptional Inhibition by a Glucocorticoid Receptor–β–Galactosidase Fusion Protein," *Cell* 65:1109–1114 (1989).

Palmiter and Brinster, "Germ–line Transformation of Mice," *Ann. Rev. Genet.* 20:465 (1986).

Pfahl, M., "Nuclear Receptor/AP–1 Interaction," *Endocrine Reviews* 14:651–658 (1993).

Picard et al., "Signal transduction by steroid hormones: nuclear localization is differentially regulated in estrogen and glucocorticoid receptors," *Cell Regulation* 1:291–299 (1990).

Pratt et al., "The hsp56 Immunophilin Component of Steroid Receptor Heterocomplexes: Could This be the Elusive Nuclear Localization Signal–Binding Protein?" *J. Steroid Biochem. Molec. Biol.* 3:269–279 (1993).

Rao and Slotman, "Endocrine Factors in Common Epithelial Ovarian Cancer," *Endocrine Reviews* 12:14–26 (1991).

Ray and Prefontaine, "Physical association and functional antagonism between the p65 subunit of transcription factor NF-$_k$B and the glucocorticoid receptor," *Proc. Natl. Acad. Sci. USA* 91:752–756 (1994).

Rexin et al., "Structure of the Glucocorticoid Receptor in Intact Cells in the Absence of Hormone," *J. Biol. Chem.* 267:9619–9621 (1992).

Sanchez et al., "Hormone–free Mouse Glucocorticoid Receptors Overexpressed in Chinese Hamster Ovary Cells are Localized to the Nucleus and Are Associated with Bolth hsp70 and hsp90," *J. Biol. Chem.* 265:20123–20130 (1990).

Sanchez et al., "Evidence that the 90–kDa phosphoprotein Associated with the Untransformed L–cell Glucocorticoid Receptor is a Murine Heat Shock Protein," *J. Biol. Chem.* 260:12398–12401 (1985).

Sanchez et al., "Relationship of the 90–kDa Murine Heat Shock Protein to the Untransformed and Transformed States of the L Cell Glucocorticoid Receptor," *J. Biol. Chem.* 262:6986–6991 (1987).

Sanchez, E., "Hsp56: A Novel Heat Shock Protein Associated with Untransformed Steroid Receptor Complexes," *J. Biol. Chem.* 265:22067–22070 (1990).

Schule et al., "Functional Antagonism between Oncoprotein c–Jun and the Glucocorticoid Receptor," *Cell* 62:1217–1226 (1990).

Schule and Evans, "Cross–coupling of signal transduction pathways: zinc finger meets leucine zipper," *Trends in Genetics* 7:377–381 (1991).

Seed and Sheen, "A simple phase–extraction assay for chloramphenicol acyltransferase activity," *Gene* 67:271–277 (1988).

Smith and Toft, "Steroid Receptors and Their Associated Proteins," *Molecular Endocrinology* 7:4–11 (1993).

Stromstedt et al., "The Glucocorticoid Receptor Binds to a Sequence Overlapping the TATA Box of the Human Osteocalcin Promoter: a Potential Mechanism for Negative Regulation," *Mol. Cell. Biol.* 3379–3383 (1991).

Sunderland and Osborne, "Tamoxifen in Premenopausal Patients with Metastatic Breast Cancer: A Review," *J. Clinical Oncology* 9:1283–1297 (1991).

Touray et al., "Characteristics of functional inhibition of the glucocorticoid receptor by Fos/Jun," *Oncogene* 6:1227–1234 (1991).

Tsai et al., "Cooperative Binding of Steroid Hormone Receptors Contributes to Transcriptional Synergism at Target Enhancer Elements," *Cell* 57:443–448 (1989).

Tsai et al., "Molecular Interactions of Steroid Hormone Receptor with its Enhancer Element: Evidence for Receptor Dimer Formation," *Cell* 55:361–369 (1988).

Tverberg and Russo, "Cell–specific Glucocorticoid Repression of Calcitonin/Calcitonin Gene–related Peptide Transcription," *J. Biol. Chem.* 267:17567–17573 (1992).

Umesono and Evans, "Determinants of Target Gene Specificity for Steroid/Thyroid Hormone Receptors," *Cell* 57:1139–1146 (1989)

Vegeto et al., "The Mechanism of RU486 Antagonism Is Dependent on the Conformation of the Carboxy–Terminal Tail of the Human Progesteron Receptor," *Cell* 69:703–713 (1992).

Ward, *Nucleic Acids Research* 18:5319 (1990).

Webster et al., "The Hormone–Binding Domains of the Estrogen and Glucocorticoid Receptors Containing an Inducible Transcription Activation Function," *Cell* 54:199–207 (1988).

Yang–Yen et al., "Transcriptional Interference between c–Jun and the Glucocorticoid Receptor: Mutual Inhibition of DNA Binding Due to Direct Protein–Protein Interaction," *Cell* 62:1205–1215 (1990).

Yem et al. "The Hsp56 Component of Steroid Receptor Complexes Binds to Immobilized FK506 and Shows Homology to FKBP–12 and FKBP–13," *J. Biol. Chem.* 267:2868–2871 (1992).

Braselmann et al., "A selective transcriptional induction system for mammalian cells based on Gal4–estrogen receptor fusion proteins," *Porc. Natl. Acad. Sci. USA* 90:1657–1661 (1993).

Curiel et al., "Gene Transfer to Respiratory Epithelial Cells via the Receprot–mediated Endocytosis Pathway," *Am. J. Respir. Cell. Mol. Biol.* 6:247–252 (1992).

Uhlen and Moks, "Gene Fusions for Purpose of Expression: An Introduction." *Methods in Enzymology* 185:129–143 (1990).

Nagaya et al., "Thyroid Hormone Receptor Mutants That Cause Resistance to Thyroid Hormone," *J. Biol. Chem.* 267:13014–13019 (1992).

Wagner et al., "Transferrin–polcation–DNA complexes: The effeto fo polycations on the structure of the complex and DNA delivery to cells," *Proc. Natl. Acad. Sci. USA* 88:4255–4259 (1991).

\* cited by examiner

DNA SEQUENCE:

```
        2636
WT   ..AAC TTG CAT GAT CTT GTC AAA CAA CTT CAT CTG TAC TGC TTG..
UP-1 ..AAT TGC ATG ATC TTG TCA AAC AAC TTC ATC TGT ACT GCT TGA
```

PROTEIN SEQUENCE:

```
        879                                                891
WT   ..Asn Leu His Asp Leu Val Lys Gln Leu His Leu Tyr Cys Leu..
                                *   *
UP-1 ..Asn Cys Met Ile Leu Ser Asn Asn Phe Ile Cys Thr Ala
```

WILD TYPE   | DNA | HORMONE |   933

| hPR CONSTRUCTS | TRANSCRIPTIONAL ACTIVITY (MILLER UNITS) | | | SPECIFIC BINDING (nM) | |
|---|---|---|---|---|---|
| | − | P | RU | P | RU |
| YEphPR-B (933) | 86 | 6200 | 586 | 1.0 | 1.3 |
| UP-1 | 286 | 466 | 8050 | 0.02 | 1.6 |
| YEphPR-B879 | 166 | 242 | 5900 | 0.04 | 1.8 |
| YEphPR-B891 | 243 | 226 | 6175 | 0.03 | 1.6 |

FIG. 4

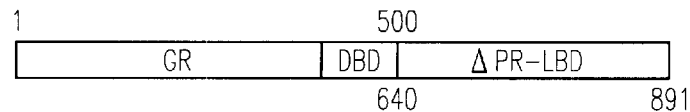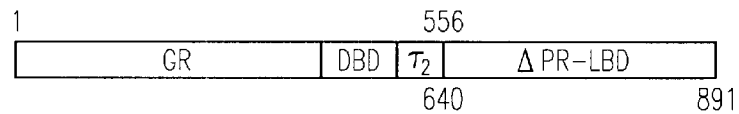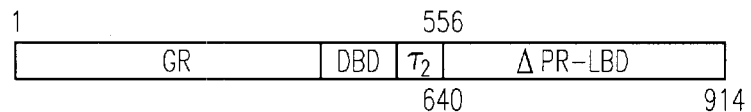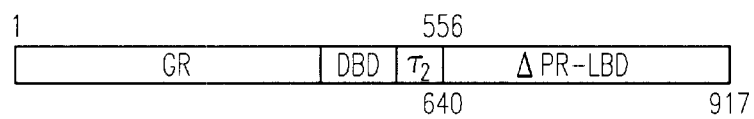
FIG. 7
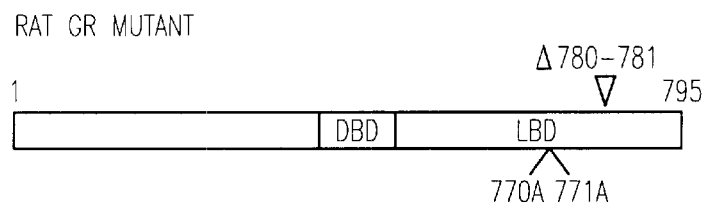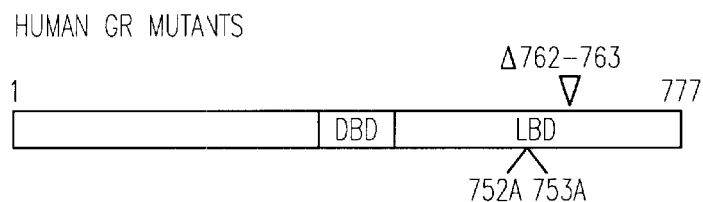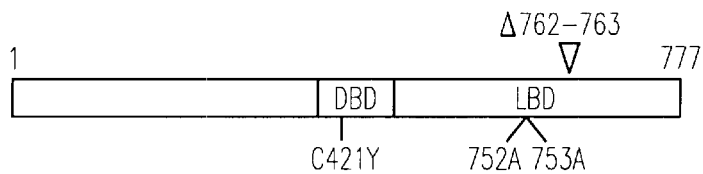
FIG. 8

ORIGIN
```
    1 ctagagtcga cctgcagccc aagctctcga gggatcctga gaacttcagg gtgagtttgg
   61 ggacccttga ttgttctttc ttttttcgcta ttgtaaaatt catgttatat ggaggggggca
  121 aagttttcag ggtgttgttt agaatgggaa gatgtccctt gtatcaccat ggaccctcat
  181 gataattttg tttctttcac tttctactct gttgacaacc attgtctcct cttattttct
  241 tttcattttc tgtaacttt tcgttaaact ttagcttgca tttgtaacga attttttaaat
  301 tcacttttgt ttatttgtca gattgtaagt acttctccta atcacttttt tttcaaggca
  361 atcagggtat attatattgt acttcagcac agttttagag aacaattgtt ataattaaat
  421 gataaggtag aatatttctg catataaatt ctggctggcg tggaaatatt cttattggta
  481 gaaacaacta catcctggtc atcatcctgc ctttctcttt atggttacaa tgatatacac
  541 tgtttgagat gaggataaaa tactctgagt ccaaaccggg cccctctgct aaccatgttc
  601 atgccttctt cttttcctta cagctcctgg caacgtgct ggttgttgtg ctgtctcatc
  661 attttggcaa agaattcact cctcaggtgc aggctgccta tcagaaggtg gtggctggtg
  721 tggccaatgc cctggctcac aaataccact gagatctttt tccctctgcc aaaaattatg
  781 gggacatcat gaagcccctt gagcatctga cttctggcta ataaaggaaa tttattttca
  841 ttgcaatagt gtgttggaat ttttgtgtc tctcactcgg aaggacatat gggagggcaa
  901 atcatttaaa acatcagaat gagtatttgg tttagagttt ggcaacatat gccatatgct
  961 ggctgccatg aacaaggtg gctataaaga ggtcatcagt atatgaaaca gcccctgct
 1021 gtccattcct tattccatag aaaagccttg acttgaggtt agatttttt tatatttgt
 1081 tttgtgttat ttttttctt aacatcccta aaattttcct tacatgtttt actagccaga
 1141 tttttcctcc tctcctgact actcccagtc atagctgtcc ctcttctctt atgaactcga
 1201 ggagcttttt gcaaaagcct aggcctccaa aaaagcctcc tcactacttc tggaatagct
 1261 cagaggccga ggcggcctcg gcctctgcat aaataaaaaa aattagtcag ccatggggcg
 1321 gagaatgggc ggaactgggc ggagttaggg gcgggatggg cggagttagg ggcgggacta
 1381 tggttgctga ctaattgaga ctgcattaat gaatcggcca acgcgcgggg agaggcggtt
 1441 tgcgtattgg gcgctcttcc gcttcctcgc tcactgactc gctgcgctcg gtcgttcggc
 1501 tgcggcgagc ggtatcagct cactcaaagg cggtaatacg gttatccaca gaatcagggg
 1561 ataacgcagg aagaacatg tgagcaaaag gccagcaaaa ggccaggaac cgtaaaaagg
 1621 ccgcgttgct ggcgtttttc cataggctcc gccccctga cgagcatcac aaaaatcgac
 1681 gctcaagtca gaggtggcga aacccgacag gactataaag ataccaggcg tttccccctg
 1741 gaagctccct cgtgcgctct cctgttccga ccctgccgct taccggatac ctgtccgcct
 1801 ttctcccttc gggaagcgtg gcgctttctc aatgctcacg ctgtaggtat ctcagttcgg
 1861 tgtaggtcgt tcgctccaag ctgggctgtg tgcacgaacc ccccgttcag cccgaccgct
 1921 gcgccttatc cggtaactat cgtcttgagt ccaacccggt aagacacgac ttatcgccac
 1981 tggcagcagc cactggtaac aggattagca gagcgaggta tgtaggcggt gctacagagt
 2041 tcttgaagtg gtggcctaac tacggctaca ctagaaggac agtatttggt atctgcgctc
 2101 tgctgaagcc agttaccttc ggaaaaagag ttggtagctc ttgatccggc aaacaaacca
 2161 ccgctggtag cggtggtttt tttgtttgca agcagcagat tacgcgcaga aaaaaaggat
 2221 ctcaagaaga tcctttgatc ttttctacgg ggtctgacgc tcagtggaac gaaaactcac
 2281 gttaagggat tttggtcatg agattatcaa aaaggatctt cacctagatc cttttaaatt
 2341 aaaaatgaag ttttaaatca atctaaagta tatatgagta aacttggtct gacagttacc
 2401 aatgcttaat cagtgaggca cctatctcag cgatctgtct atttcgttca tccatagttg
 2461 cctgactccc cgtcgtgtag ataactacga tacggagggg cttaccatct ggccccagtg
 2521 ctgcaatgat accgcgagac ccacgctcac cggctccaga tttatcagca ataaaccagc
 2581 cagccggaag ggccgagcgc agaagtggtc ctgcaacttt atccgcctcc atccagtcta
 2641 ttaattgttg ccgggaagct agagtaagta gttcgccagt taatagtttg cgcaacgttg
 2701 ttgccattgc tacaggcatc gtggtgtcac gctcgtcgtt tggtatggct tcattcagct
 2761 ccggttccca acgatcaagg cgagttacat gatcccccat gttgtgcaaa aaagcggtta
 2821 gctccttcgg tcctccgatc gttgtcagaa gtaagttggc cgcagtgtta tcactcatgg
 2881 ttatggcagc actgcataat tctcttactg tcatgccatc cgtaagatgc ttttctgtga
 2941 ctggtgagta ctcaaccaag tcattctgag aatagtgtat gcggcgaccg agttgctctt
 3001 gcccggcgtc aatacgggat aataccgcgc cacatagcag aactttaaaa gtgctcatca
 3061 ttggaaaacg ttcttcgggg cgaaaactct caaggatctt accgctgttg agatccagtt
 3121 cgatgtaacc cactcgtgca cccaactgat cttcagcatc ttttactttc accagcgttt
 3181 ctgggtgagc aaaaacagga aggcaaaatg ccgcaaaaaa gggaataagg gcgacacgga
 3241 aatgttgaat actcatactc ttcctttttc aatattattg aagcatttat cagggttatt
 3301 gtctcatgag cggatacata tttgaatgta tttagaaaaa taaacaaata ggggttccgc
 3361 gcacatttcc ccgaaaagtg ccacctgacg tctaagaaac cattattatc atgacattaa
```

FIG. 9A

```
3421 cctataaaaa taggcgtatc acgaggccct ttcgtcttca agctgcctcg cgcgtttcgg
3481 tgatgacggt gaaaacctct gacacatgca gctcccggag acggtcacag cttgtctgta
3541 agcggatgcc gggagcagac aagcccgtca gggcgcgtca gcgggtgttg gcgggtgtcg
3601 gggcgcagcc atgacccagt cacgtagcga tagcggagtt ggcttaacta tgcggcatca
3661 gagcagattg tactgagagt gcaccatatc gacgctctcc cttatgcgac tcctgcatta
3721 ggaagcagcc cagtagtagg ttgaggccgt tgagcaccgc cgccgcaagg aatggtgctg
3781 gcttatcgaa attaatcgac tcactatagg gagacccgaa ttcgagctcg ccccgttaca
3841 taacttacgg taaatggccc gcctggctga ccgcccaacg accccgccc attgacgtca
3901 ataatgacgt atgttcccat agtaacgcca atagggactt tccattgacg tcaatgggtg
3961 gagtatttac ggtaaactgc ccacttggca gtacatcaag tgtatcatat gccaagtacg
4021 ccccctattg acgtcaatga cggtaaatgg cccgcctggc attatgccca gtacatgacc
4081 ttatgggact ttcctacttg gcagtacatc tacgtattag tcatcgctat taccatggtg
4141 atgcggtttt ggcagtacat caatgggcgt ggatagcggt ttgactcacg gggatttcca
4201 agtctccacc ccattgacgt caatgggagt ttgttttggc accaaaatca acgggacttt
4261 ccaaaatgtc gtaacaactc cgccccattg acgcaaatgg gcggtaggcg tgtacggtgg
4321 gaggtctata taagcagagc tcgtttagtg aaccgtcaga tcgcctggag acgccatcca
4381 cgctgttttg acctccatag aagacaccgg gaccgatcca gcctccgcgg gatcttggtg
4441 gcgtgaaact cccgcacctc ttcggccagc gccttgtaga agcgcgtatg gcttcgtggg
4501 gatcccccaa agaatcctta gctcccctg gtagagacga agtccctggc agtttgcttg
4561 gccaagggag ggggagcgta atggactttt ataaaagcct gaggggagga gctacagtca
4621 aggtttctgc atcttcgccc tcagtggctg ctgcttctca ggcagattcc aagcagcaga
4681 ggattctcct tgatttctcg aaaggctcca caagcaatgt gcagcagcga cagcagcagc
4741 agcagcagca gcagcagcag cagcagcagc agcagcagca gcagcagcca ggcttatcca
4801 aagccgtttc actgtccatg gggctgtata tgggagagac agaaacaaaa gtgatgggga
4861 atgacttggg ctacccacag cagggccaac ttggcctttc ctctggggaa acagactttc
4921 ggcttctgga agaaagcatt gcaaacctca ataggtcgac cagcgttcca gagaacccca
4981 agagttcaac gtctgcaact gggtgtgcta ccccgacaga gaaggagttt cccaaaactc
5041 actcggatgc atcttcagaa cagcaaaatc gaaaaagcca gaccggcacc aacggaggca
5101 gtgtgaaatt gtatcccaca gaccaaagca cctttgacct cttgaaggat ttggagtttt
5161 ccgctgggtc cccaagtaaa gacacaaacg agagtccctg gagatcagat ctgttgatag
5221 atgaaaactt gctttctcct ttggcgggga aagatgatcc attccttctc gaagggaaca
5281 cgaatgagga ttgtaagcct cttattttac cggacactaa acctaaaatt aaggatactg
5341 gagatacaat cttatcaagt cccagcagtg tggcactacc caagtgaaa acagaaaaag
5401 atgatttcat tgaactttgc accccgggg taattaagca agagaaactg ggcccagttt
5461 attgtcaggc aagcttttct gggacaaata taattggtaa taaaatgtct gccatttctg
5521 ttcatggtgt gagtacctct ggaggacaga tgtaccacta tgacatgaat acagcatccc
5581 tttctcagca gcaggatcag aagcctgttt ttaatgtcat tccaccaatt cctgttggtt
5641 ctgaaaactg gaataggtgc caaggctccg gagaggacag cctgacttcc ttggggggctc
5701 tgaacttccc aggccggtca gtgtttttcta atgggtactc aagccctgga atgagaccag
5761 atgtaagctc tcctccatcc agctcgtcag cagccacggg accacctccc aagctctgcc
5821 tggtgtgctc cgatgaagct tcaggatgtc attacggggt gctgacatgt ggaagctgca
5881 aagtattctt taaaagagca gtggaaggac agcacaatta cctttgtgct ggaagaaacg
5941 attgcatcat tgataaaatt cgaaggaaaa actgcccagc atgccgctat cggaaatgtc
6001 ttcaggctgg aatgaacctt gaagctcgaa aaacaaagaa aaaaatcaaa gggattcagc
6061 aagccactgc aggagtctca caagacactt cggaaaatcc taacaaaaca atagttcctg
6121 cagcattacc acagctcacc cctaccttgg tgtcactgct ggaggtgatt gaacccg
```

*FIG. 9B*

| RECEPTOR | TREATMENT | pg CAT PROTEIN INDUCED | NORMALIZED TO CONTROL |
|---|---|---|---|
| WILD-TYPE hGR | CONTROL | 0.4 | 1 |
| | DEX | 64.4 | 161 |
| | RU | 1.4 | 3.5 |
| GRPR FUSION | CONTROL | 0.9 | 1 |
| | DEX | 0.6 | 0.7 |
| | RU | 5.4 | 6 |
| WILD-TYPE RAT GR | CONTROL | 2.2 | 1 |
| | DEX | 26.4 | 12 |
| | RU | 6.3 | 2.9 |
| CS1.CD | CONTROL | 2.2 | 1 |
| | DEX | 1.8 | 0.8 |
| | RU | 29.6 | 13.5 |

US 6,416,998 B1

PLASMID ENCODING A MODIFIED STEROID HORMONE

RELATED APPLICATIONS

This application is a continuation-in-part of U.S. application Ser. No. 07/939,246, Vegeto, et al., filed Sep. 2, 1992, entitled "Mutated Steroid Hormone Receptors, Methods for Their Use and Molecular Switch for Gene Therapy," now abandonded, the whole of which (including drawings) is hereby incorporated by reference. In addition, this application is related to U.S. Pat. No. 5,364,791, Vegeto, et al., issued Nov. 15, 1994, entitled "Progesterone Receptor Having C-Terminal Hormone Binding Domain Truncations," and PCT/US93/04399 the whole of which (including drawings) are both hereby incorporated by reference.

BACKGROUND OF THE INVENTION

This invention relates to gene therapy whereby modified steroid receptors regulate the expression of genes within tissue.

Intracellular receptors are a superfamily of related proteins that mediate the nuclear effects of steroid hormones, thyroid hormone and vitamins A and D (Evans, *Science* 240:889–895 (1988)). The cellular presence of a specific intracellular receptor defines that cell as a target for the cognate hormone. The mechanisms of action of the intracellular receptors are related in that they remain latent in the cytoplasm or nuclei of target cells until exposed to a specific ligand (Beato, *Cell* 56:335–344 (1989); O'Malley, et al., *Biol. Reprod.* 46:163–167 (1992)). Interaction with hormone then induces a cascade of molecular events that ultimately lead to the specific association of the activated receptor with other proteins or regulatory elements of target genes. The resulting positive or negative effects on regulation of gene transcription are determined by the cell-type and promoter-context of the target gene.

In the case of steroid hormones and steroid receptors, such complexes are responsible for the regulation of complex cellular events, including activation or repression of gene transcription. For example, the ovarian hormones, estrogen and progesterone, are responsible, in part, for the regulation of the complex cellular events associated with differentiation, growth and functioning of female reproductive tissues. Likewise, testosterone is responsible for the regulation of complex cellular events associated with differentiation growth and function of male reproductive tissues.

In addition, these hormones play important roles in development and progression of malignancies of the reproductive endocrine system. The reproductive steroids estrogen, testosterone, and progesterone are implicated in a variety of hormone-dependent cancers of the breast (Sunderland, et al., *J. Clin. Oncol.* 9:1283–1297 (1991)), ovary (Rao, et al., *Endocr. Rev.* 12:14–26 (1991)), endometrium (Dreicer, et al., *Cancer Investigation* 10:27–41, (1992)), and possibly prostate (Daneshgari, et al., *Cancer* 71:1089–1097 (1993)). In addition, the onset of post-menopausal osteoporosis is related to a decrease in production of estrogen (Barzel, *Am. J. Med.* 85:847–850 (1988)).

In addition, corticosteroids are potent and well-documented mediators of inflammation and immunity. They exert profound effects on the production and release of numerous humoral factors and the distribution and proliferation of various cellular components associated with the immune and inflammatory responses. For example, steroids are able to inhibit the production and release of cytokines (IL-1, IL-2, IL-3, IL-6, IL-8, TNF-α, IFN-γ), chemical mediators (eicosinoids, histamine), and enzymes (MMPs) into tissues, and directly prohibit the activation of macrophages and endothelial cells. Due to the global down-regulation of these physiological events, corticosteroids have a net effect of suppressing the inflammatory response and have therefore been used extensively to treat a variety of immunological and inflammatory disorders (rheumatoid arthritis, psoriasis, asthma, allergic rhinitis, etc.).

Besides the therapeutic benefits, however, there are some severe toxic side effects associated with steroid therapy. These include peptic ulcers, muscle atrophy, hypertension, osteoporosis, headaches, etc. Such side effects have hindered the utilization of steroids as therapeutic agents.

In general, the biological activity of steroid hormones is mediated directly by a hormone and tissue-specific intracellular receptor. Ligands are distributed through the body by the hemo-lymphatic system. The hormone freely diffuses across all membranes but manifests its biological activity only in those cells containing the tissue-specific intracellular receptor.

In the absence of ligand, the inactive steroid hormone receptors such as the glucocorticoid ("GR"), mineral corticoid ("MR"), androgen ("AR") progesterone ("PR") and estrogen ("ER") receptors are sequestered in a large complex consisting of the receptor, heat-shock proteins ("hsp") 90, hsp70 and hsp56 and other proteins as well. Smith, et al., *Mol. Endo.* 7:4–11 (1993). The cellular localization of the physiologically inactive form of the oligomeric complex has been shown to be either cytoplasmic or nuclear. Picard, et al., *Cell Regul.* 1:291–299 (1992); Simmons, et al., *J. Biol. Chem.* 265:20123–20130 (1990).

Upon binding its agonist or antagonist ligand, the receptor changes conformation and dissociates from the inhibitory heteroligomeric complex. Allan, et al., *J. Biol. Chem.* 267:19513–19520 (1992); Allan, et al., *P.N.A.S.* 89:11750–11754 (1992). In the case of GR and other related systems such as AR, MR, and PR, hormone binding elicits a dissociation of heat shock and other proteins and the release of a monomeric receptor from the complex. O'Malley, et al., *Biol. Reprod.* 46:163–167 (1992). Studies from genetic analysis and in vitro protease digestion experiments show that conformational changes in receptor structure induced by agonists are similar but distinct from those induced by antagonists. Allan, et al., *J. Biol. Chem.* 267:19513–19520 (1992); Allan, et al., *P.N.A.S.* 89:11750–11754 (1992); Vegeto, et al., *Cell* 69:703–713 (1992). However, both conformations are incompatible with hsp-binding.

Following the conformation changes in receptor structure, the receptors are capable of interacting with DNA. Studies suggest that the DNA binding form of the receptor is a dimer. In the case of GR homodimers, Tsai, et al., *Cell* 55:361–369 (1988), this allows the receptor to bind to specific DNA sites in the regulatory region of target gene promoters. Beato, *Cell* 56:335–344 (1989). These short nucleotide sketches are arranged as palindromic, inverted or repeated repeats. Id. Specificity is determined by the sequence and the spacing of the repeated sequences. Umesono, et al., *Cell* 57:1139–1146. Following binding of the receptor to DNA, the hormone is responsible for mediating a second function that allows the receptor to interact specifically with the transcription apparatus. Such interaction could either provide positive or negative regulation of gene expression, i.e., steroid receptors are ligand-binding transcription factors, capable of not only activating but also repressing the expression of specific genes. Studies have shown, however, that repression does not require DNA binding.

For instance, when bound to their intracellular receptors, corticosteroids can affect the transcription of a variety of genes whose products play key roles in the establishment and progression of an inflamed situation. Such genes include those encoding for cytokines, chemical mediators and enzymes. Transcription of these genes can be repressed or activated depending on the transcription factors and/or regulatory sequences controlling the expression of the gene. Presently there are numerous reports documenting the effect of glucocorticoid on the expression of various genes at the transcriptional level.

In particular, the glucocorticoid receptor is a member of a family of ligand-dependent transcription factors capable of both positive and negative regulation of gene expression (Beato, *FASEB J.* 5:2044–2051 (1991); Pfahl, *Endocr. Rev.* 14:651–658, (1993); Schule, et al., *Trends Genet.* 7:377–381 (1991)). In its inactivated form, the GR is part of a large heteromeric complex which includes hsp90 as well as other proteins (Denis, et al., *J. Biol. Chem.* 262:11803–11806 (1987); Howard, et al., *J. Biol. Chem.* 263:3474–3481 (1988); Mendel, et al., *J. Biol. Chem.* 261:3758–3763 (1986); Rexin, et al., *J. Biol. Chem.* 267:9619–9621 (1992); Sanchez, et al., *J. Biol. Chem.* 260:12398–12401 (1985)), and hsp56 (Lebea, et al., *J. Biol. Chem.* 267:4281–4284 (1992); Pratt, *J. Steroid Biochem. Mol. Biol.* 46:269–279 (1993); Rexin, *J. Biol. Chem.* 267:9619–9621 (1992); Sanchez, *J. Biol. Chem.* 265:22067–22070 (1990); Yem, *J. Biol. Chem.* 267:2868–2871, (1992)). Binding of agonist stimulates receptor activation, dissociation from hsp90 and the other proteins (Denis, et al., *Nature* 333:686–688 (1988); Sanchez, et al., *J. Biol. Chem.* 262:6986–6991 (1987)), and nuclear translocation, prerequisites for both transactivation and transrepression.

Cloning of several members of the steroid receptor superfamily has facilitated the reconstitution of hormone-dependent transcription in heterologous cell systems and facilitated delineation of the GR activation and repression mechanisms. Subsequently, in vivo and in vitro studies with mutant and chimeric receptors have demonstrated that steroid hormone receptors are modular proteins organized into structurally and functionally defined domains. Deletion mutants of the GR have determined that the transactivation domain is located at the N-terminal amino acid sequence positioned between amino acids 272 and 400. Jonat, et al., *Cell* 62:1189–1204 (1990). A well defined 66 amino acid DNA binding domain ("DBD") has been identified and studied in detail, using both genetic and biochemical approaches. Lucibello, et al., *EMBO J.* 9:2827–2834 (1990). The ligand or hormone binding domain ("LBD"), located in the carboxyl-terminal portion of the receptor, consists of about 300 amino acids. Kerppola, et al., *Mol. Cell. Biol.* 13:3782–3791 (1993). The LBD has not been amenable to detailed site-directed mutagenesis, since this domain appears to fold into a complex tertiary structure, creating a specific hydrophobic pocket which surrounds the effector ligand when bound. This feature creates difficulty in distinguishing among amino acid residues that affect the overall structure of the LBD domain from those involved in a direct contact with the ligand. The LBD also contains sequences responsible for receptor dimerization, nuclear localization, hsp interactions and transactivation sequences of the receptor. Fuller, et al, *FASEB J.* 5:3092–3099 (1991).

The mechanism of gene activation is far better understood than that of repression. For transactivation, a ligand-induced conformational change, comparable to that inferred to be necessary for activation of the progesterone (Allan, et al., *Proc. Natl. Acad. Sci. USA* 35 89:11750–11754 (1992)) and estrogen (Beekman, et al., *Mol. Endocrinol.* 7:1266–1274 (1993)) receptors, is required for efficient activation of the transcription activating function of the receptor (Hollenberg and Evans, *Cell* 55:899–906 (1988); Webster, et al., *Cell* 54:199–207, (1988)). Furthermore, the conformational change is required for interaction of the receptor with other components of the transcription apparatus. Transactivation is mediated by a receptor dimer bound to a glucocorticoid response element ("GRE"). Such transactivation occurs exclusively by homodimerization. This is mainly achieved by a region in the second zinc finger of the receptor known as the D-loop. Umesono, et al., *Cell* 57:1139–1146 (1989); Dahlman-Wright, et al., *J. Biol. Chem.* 266:3107–3112 (1991). The resulting homodimers then bind to the palindromic GRE to initiate the transcriptional activation process. Evans, *Science* 240:889–895 (1988); Cato, et al.; *J. Steroid Biochem. Mol. Biol.* 43:63–68 (1992).

Transrepression, on the other hand, appears to be mediated by the monomeric form of the receptor through interactions with other transcriptional factors, including AP-1 and $NF_K$-B, preventing them from carrying out their function as transcriptional activators. Hoeck, et al., *EMBO J.* 13:4087–4095 (1994). Studies also show transrepression by the dimeric form of the receptor. In the case of the monomeric pathway, studies suggest that AP-1 prevents hormone-dependent activation of GR-regulated promoters through a mutually inactive complex formed either by a direct protein-protein interaction of the receptor and AP-1 or through a third partner. Miner, et al., *Cell Growth Differ.* 2:525–530 (1991); Pfahl, *Endocrine Rev.* 14:651–658 (1993). Such transrepression of AP-1 and $NF_K$-B mediated by the monomeric form of the receptor depends on the presence of the DNA binding domain. It does not depend on the ability of the receptor to bind DNA. In the case of the dimeric form of the receptor, several studies suggest mechanisms for such GR-mediated transrepression include GR binding to a sequence overlapping a cis-acting element for another trans-acting factor, thereby displacing it from, or preventing its binding to, its cognate element (Akerblom, et al., *Science* 241:350–353 (1988); Drouin, et al., *Mol. Cell. Biol.* 9:5305–5314 (1989); Oro, et al., *Cell* 55:1109–1114, (1988); Stromstedt, et al., *Mol. Cell. Biol.* 11:3379–3383, (1991)).

As noted above, GR-mediated transrepression attributed to direct or indirect interaction of the GR with other trans-acting factors, results in inhibition of their activity and/or ability to bind to DNA (Celada, et al., *J. Exp. Med.* 177:691–698 (1993); Diamond, et al., *Science* 249:1266–1272 (1990); Gauthier, et al., *Embo J.* 12:5089–5096 (1993); Jonat, et al., *Cell* 62:1189–1204 (1990); Kutoh, et al., *Mol. Cell Biol.* 12:4955–4969 (1992); Lucibello, et al., *Embo J.* 9:2827–2834 (1990); Ray, et al., *Proc. Natl. Acad. Sci. USA* 91:752–756 (1994); Schule, et al., *Cell.* 62:1217–1226 (1990); Tverberg, et al., *J. Biol. Chem.* 267:17567–17573 (1992); Yang-Yen, et al., *Cell* 62:1205–1215 (1990); Lucibello, et al., *EMBO J.* 9:2827–2834 (1990)). These models require ligand binding to stimulate receptor activation, dissociation from hsp90, and nuclear translocation. It is not clear whether these mechanisms are dependent on the same ligand-induced conformational change needed for transactivation. However, a transactivation-defective mutant represses the AP-1 dependent promoter suggesting that the transactivation function of the receptor is not required for the repression of AP-1 activity. Yang-Yen, et al., *Cell* 62:1205–1215 (1990). Furthermore, similar studies also suggest that the transactivation function of the receptor is not required for the repression of NF$_K$-B activity.

In attempts to decipher the transrepression mechanism, studies have reviewed the role of the bound ligand in GR-mediated repression of AP-1-responsive genes containing a tetradecanoyl phorbol acetate ("TPA") response element. Repression of these genes has been proposed to be the result of the direct interaction of the GR with c-Jun (Diamond, et al., *Science* 249:1266–1272 (1990); Lucibello, et al., *EMBO J.* 9:2827–2834 (1990); Schule, et al., *Cell* 62:1217–1226 (1990); Touray, et al., *Oncogene* 6:1227–1234 (1991); Yang-Yen, et al., *Cell* 62:1205–1215 (1990) ) or c-Fos (Kerppola, et al., *Mol. Cell. Biol.* 13:3782–3791 (1992)) which are components of the AP-1 transcription complex. The GR DNA-binding domain is necessary for this interaction, since most mutations in this domain result in the loss of repressor activity in vivo (Diamond, et al., *Science* 249:1266–1272 (1990); Jonat, et al., *Cell* 62:1189–1204 (1990); Lucibello, et al., *EMBO J.* 9:2827–2834 (1990); Schule, et al., *Cell* 62:1217–1226 (1990); Yang-Yen, et al., *Cell* 62:1205–1215 (1990)).

The DNA-binding domain is also necessary for inhibition of in vitro transcription from the collagenase promoter and inhibition of Jun-Fos heterodimer binding to the collagenase TPA response element (Mordacq, et al., *Genes Dev.* 3:760–769 (1989)). However, deletion or truncation of the ligand-binding domain also results in a significant loss of repressor activity (Jonat, et al., *Cell* 62:1189–1204 (1990); Schule, et al., *Cell* 62:1217–1226 (1990); Yang-Yen, et al., *Cell* 62:1205–1215 (1990)), suggesting that the ligand-binding domain may contribute to, or modulate, the inhibition of AP-1 activity.

Further studies examining the role of the ligand in GR-mediated transrepression of the collagenase promoter found efficient receptor-mediated transrepression with ligand-free mutant GR in which the first cysteine residue of the proximal zinc finger was replaced with tyrosine. Liu, et al., *Mol. Cell. Bio.* 15:1005–1013 (1995). Such studies suggest that neither retention of the ligand nor direct binding of the receptor to DNA is required, i.e., that transrepression of AP-1 activity by GR is ligand independent.

SUMMARY OF THE INVENTION

Applicants have determined that it is useful to construct modified steroid hormone receptors which regulate the expression of nucleic acid sequences. Specifically, these modifications allow control of the transactivation and transrepressing functions of the modified steroid hormone receptor. Such modifications allow the receptors to bind various ligands whose structures differ dramatically from the naturally-occurring ligands. This includes the binding of non-natural ligands, anti-hormones and non-native ligands.

These modifications are generated in the ligand binding domain of the GR and eliminate the ability of the GR to bind its natural ligand. These modified steroid receptors exhibit normal transactivation and transrepression activity; however, stimulation of such activity occurs via activation by a non-natural and exogenously or endogenously applied ligand. Modifications are also generated in the ligand binding domain of the PR and eliminate the ability of PR to bind its natural ligand. Replacement of the GR binding domain with the modified PR binding domain allows the stimulation of GR responsive gene expression via non-natural ligands.

Other modifications to the GR ligand binding domain in conjunction with modifications to the DNA binding domain of GR eliminate the ability of steroid hormones to initiate transactivation by its natural ligand. Instead, such modifications allow the modified receptor to bind non-natural ligands and stimulate the transrepression regulation of gene expression but not transactivation. Likewise, using the same ligand binding domain modification in conjunction with modifications to the transregulatory domain allows the modified receptor to bind non-natural ligands and stimulate transactivation but not transrepression of gene expression.

Other modifications remove the ligand binding domain completely to create a constitutively active steroid receptor. Such modifications cause continual transactivation and transrepression effects on the regulation of gene transcription. In addition, modifications that selectively eliminate either transactivation or transrepression functions are incorporated into the constitutively active steroid receptor thereby constitutively transrepressing or transactivating gene expression. Furthermore, other modifications use a ligand binding domain which recognizes its natural ligand or if modified recognizes a non-natural ligand, but is fused with a DNA binding domain and transregulatory domains not associated normally with the ligand binding domain. Such a construct is capable of regulating the expression of a gene not normally associated with the ligand binding domain in a wild type receptor protein.

These modified receptors can be expressed by specially designing DNA expression vectors to control the level of expression of recombinant gene products. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either activate or repress transcription.

These receptors are modified to allow them to bind various ligands whose structure is either naturally occurring or differs from naturally occurring ligands. By screening receptor mutants, receptors can be selected that respond to ligands which do not activate the host cell endogenous receptor. Thus, regulation of a desired transgene can be achieved using a ligand which binds to and regulates a customized receptor. This occurs only with cells that have incorporated and express the modified receptor.

Taking advantage of the abilities of the modified steroid hormone receptor to effect regulation of gene expression, these gene constructs can be used as therapeutic gene medicines. These modified receptors are useful in gene therapy where the level of expression of a gene, whether transactivation or repression, is required to be controlled. The number of diseases associated with inappropriate production or responses to hormonal stimuli highlights the medical and biological importance of these constructs.

The properties of the modified steroid hormone receptors allow the deleterious effects of steroids to be avoided while maintaining their therapeutic benefits. In particular, administration of steroids causes toxicity problems. The deleterious effects of steroids can be attributed to the in vivo transactivation or transrepression of certain genes. These toxic effects may well be the result of both transactivation and transrepression, or be primarily attributable to one of them. The present invention features the use of modified GR molecules as gene medicines for the replacement of steroid therapy. These synthetic receptors retain functions similar to those of the endogenous receptors, but by responding to alternative ligands, eliminate some of the toxic side effects attributable to currently used steroid therapy.

This ability of the GR constructs to avoid steroid toxicity but still exhibit therapeutic effects allows the constructs to be used for treating numerous diseases, including arthritis, asthma, senile dementia or Parkinson's disease. Furthermore, the constructs can be used for preventing or treating diseases in which inappropriate production or responses to hormonal stimuli exists, e.g., hormone-dependent cancers of the breast, ovary, endometrium, prostate, and post-menopausal osteoporosis. The constructs also can be used in conjunction with co-transfected expression vectors so as to operate as a gene switch. For detailed description of gene switch, see, U.S. application Ser. No. 07/939,246, Vegeto et al., and U.S. Pat. No. 5,364,791, Vegeto et al., the whole of which (including drawings) are both hereby incorporated by reference.

In addition, the constructs above can be used for gene replacement therapy in humans and for creating transgenic animal models used for studying human diseases. The transgenic models can be used as well for assessing and exploring novel therapeutic avenues to treat effects of chemical and physical carcinogens and tumor promoters. The above constructs can also be used for distinguishing steroid hormone receptor antagonists and steroid hormone receptor agonists. Such recognition of antagonist or agonist activity can be performed using cells transformed with the above constructs.

In a first aspect, the present invention features a modified glucocorticoid receptor fusion protein. The fusion protein receptor is GR with its ligand-binding domain replaced with a mutated PR ligand-binding domain. This fusion protein is capable of being activated by the binding of a non-natural ligand but not by natural or synthetic glucocorticoid or other natural or synthetic steroids. The fusion protein includes a glucocorticoid receptor region which comprises a DNA binding domain and transregulatory domains. The transregulatory domains are capable of transactivating or transrepressing glucocorticoid responsive gene expression. Such mutations and fusion proteins can be created from different receptors and from different species, and still accomplish the same physiological effect. Thus, the present invention is not limited to glucocorticoid receptors nor to the species herein.

In addition to the glucocorticoid receptor region, the fusion protein also includes a mutated progesterone ligand binding region which is capable of binding a non-natural ligand. The mutated ligand binding region is mutated by deletion of about 42 to 54 carboxyl terminal amino acids of a progesterone receptor ligand binding domain. The mutated progesterone receptor ligand binding region comprises about amino acids 640 through 891 of a progesterone receptor. Other embodiments comprise amino acids 640–917 while other embodiments comprise amino acids 640–920. One skilled in the art will recognize that various mutations can be created to achieve the desired function.

The term "fusion protein" as used herein refers to a protein which is composed of two or more proteins, or fragments thereof, occurring separately in nature. The combination can be between complete amino acid sequences of the protein as found in nature, or fragments thereof. In the case of the glucocorticoid-progesterone fusion protein receptor, the fusion protein is composed of portions of the glucocorticoid receptor and the progesterone receptor. This combination can include the complete amino acid sequence of each protein or fragments thereof. For example, the glucocorticoid-progesterone fusion protein may include the ligand binding domain of progesterone and the DNA binding domain and transregulatory domains of the glucocorticoid receptor. This is only an example and not meant to be limiting.

In addition to the above, other fusion proteins can be constructed. A useful construct includes a fusion protein comprising: (1) a ligand binding domain which binds endogenous ligand, and (2) a DNA binding domain and/or transregulatory domains not naturally associated with the ligand binding domain. Such a construct allows the regulation of expression of other genes, whether activation or repression, which are not normally regulated by the ligand binding domain. A person skilled in the art will recognize that there are other possible variations of the above fusion protein that are within the scope of the present invention.

The term "non-natural ligand" as used herein refers to compounds which can normally bind to the ligand binding domain of a receptor but are not the endogenous ligand. The receptor is not exposed to the ligand unless it is exogenously supplied. This also includes ligands or compounds which are not normally found in animals or humans. Non-natural also includes ligands which are not naturally found in the specific organism (man or animal) in which gene therapy is contemplated. These ligands activate receptors by binding to the modified ligand binding domain. Activation can occur through a specific ligand-receptor interaction whether it is through direct binding or through association in some form with the receptor.

"Natural ligand" as used here refers to compounds which normally bind to the ligand binding domain of a receptor and are endogenous. The receptor in this case is exposed to the ligand endogenously. Natural ligands include steroids, retinoids, fatty acids, vitamins, thyroid hormones, as well as synthetic variations of the above. This is meant to be only an example and non-limiting.

The term "ligand" as referred to herein means any compound which activates the receptor, usually by interaction with the ligand binding domain of the receptor. Ligand includes a molecule or an assemblage of molecules capable of specifically binding to a modified receptor. The term "specifically binding" means that a labelled ligand bound to the receptor can be completely displaced from the receptor by the addition of unlabelled ligand, as is known in the art.

Examples of non-natural ligands and non-native ligands include the following: 11β-(4-dimethylaminophenyl)-17β-hydroxy-17α-propinyl-4,9-estradiene-3-one (RU486 or Mifepripeestone); 11β-(4-dimethylaminophenyl)-17α-hydroxy-17β-(3-hydroxypropyl)-13α-methyl-4,9-gonadiene-3-one (ZK98299 or Onapristone); 11β-(4-acetylphenyl)-17α-hydroxy-17α-(1-propinyl)-4,9-estradiene-3-one (ZK112993); 11α-(4-dimethylaminophenyl)-17β-hydroxy-17α-(3-hydroxy-1(Z)-propenyl-estra-4,9-diene-3-one (ZK-98734); (7β,11β,17β)-11-(4-dimethylaminophenyl)-7-methyl-4',5'-dihydrospiro [ester-4,9-diene-17,2'(3'H)-furan]-3-one (Org31806); (11β, 14β,17α)-4',5'-dihydro-11-(4-dimethylaminophenyl)-[spiroestra-4,9-diene-17,2'(3'H)-furan]-3-one (Org31376); 5α-pregnane-3,2-dione.

The term "binding" or "bound" as used herein refers to the association, attaching, connecting, or linking through covalent or non-covalent means, of a ligand, whether non-natural or natural, with a corresponding receptor. The ligand and receptor interact at complementary and specific within sites on a given structure. Binding includes, but is not limited to, components which associate by electrostatic binding, hydrophobic binding, hydrogen binding, intercalation or forming helical structures with specific sites on nucleic acid molecules.

The term "glucocorticoid receptor" refers to a steroid hormone receptor which responds to a glucocorticoid ligand. The glucocorticoid receptor is part of the steroid hormone receptor superfamily which are known steroid receptors whose primary sequence suggests that they are related to each other. Representative examples of such receptors include the estrogen, progesterone, Vitamin D, chicken ovalbumin upstream promoter transfactor, ecdysone, Nurr-1 and orphan receptors, glucocorticoid-α, glucocorticoid-β, mineralocorticoid, androgen, thyroid hormone, retinoic acid, and retinoid X. These receptors are composed of DNA binding domains, ligand binding domains, as well as transregulatory domains.

The glucocorticoid receptor is a ligand-dependent transcription factor capable of both positive and negative regulation of gene expression. Interaction of the receptor with a ligand induces a cascade of molecular events that ultimately lead to the specific association of the activated receptor with regulatory elements of target genes. In an inactive form such receptors form a large complex comprising the receptor, heat shock proteins and other proteins.

The term "glucocorticoid receptor region" refers to a fragment or part of the complete glucocorticoid receptor as defined above. A glucocorticoid receptor region may retain complete or partial activity of the natural receptor protein. For example, a glucocorticoid receptor region might contain only the DNA binding domain and the transregulatory domains and not the ligand binding domain, or vice versa. This is only an example and not meant to be limiting.

The term "ligand binding domains" or "ligand binding region" as used herein refers to that portion of a steroid hormone receptor protein which binds the appropriate hormone or ligand and induces a cascade of molecular events that ultimately leads to the specific association of the activated receptor with regulatory elements of target genes. This includes, but is not limited to, the positive or negative effects on regulation of gene transcription. Binding of ligand to the ligand binding domain induces a conformation change in the receptor structure. The conformational change includes the dissociation of heat shock proteins and the release of a monomeric receptor from the receptor complex, as well as a different tertiary or 3-dimensional structure. The conformational change that occurs is specific for the steroid receptor and ligand that binds to the ligand binding domain.

For example, for glucocorticoid receptors, the conformation change that occurs when glucocorticoid hormone binds allows homodimerization, i.e., dimerization between two identical GR molecules. However, heterodimerization can occur with other steroid receptors, i.e., dimerization with two molecules such as GR and ER. Such dimerization allows the receptor to bind with DNA or induce the regulatory effect by binding other transcription factors.

The term "DNA binding domain" as used herein refers to that part of the steroid hormone receptor protein which binds specific DNA sequence in the regulatory regions of target genes. This domain is capable of binding short nucleotide stretches arranged as palindromic, inverted or repeated repeats. Such binding, will activate gene expression depending on the specific ligand and the conformational changes due to such ligand binding. For repression, DNA binding is not needed.

The term "transregulatory domain" as used herein refers to those portions of the steroid hormone receptor protein which are capable of transactivating or transrepressing gene expression. This would include different regions of the receptor responsible for either repression or activation, or the regions of the receptor responsible for both repression and activation. Such regions are spacially distinct. The above is only an example and meant to be non-limiting. For transrepression, this domain under one mechanism is involved with dimerization which in turn causes a protein/protein interaction to prevent or repress gene expression. Such regulation occurs when the receptor is activated by the ligand binding to the ligand binding domain. The conformational change of the receptor is capable of forming a dimer with a discrete portion of the transregulatory domain to repress gene expression. In addition, repression can occur through a monomeric form of the receptor, however, DNA binding is not necessary (see below).

The terms "transactivation," "transactivate," or "transactivating" refer to a positive effect on the regulation of gene transcription due to the interaction of a hormone or ligand with a receptor causing the cascade of molecular events that ultimately lead to the specific association of the activated receptor with the regulatory elements of the target genes. Transactivation can occur from the interaction of non-natural as well as natural ligands. Agonist compounds which interact with steroid hormone receptors to promote transcriptional response can cause transactivation. Such positive effects on transcription include the binding of an activated receptor to specific recognition sequences in the promoter of target genes to activate transcription. The activated receptors are capable of interacting specifically with DNA. The hormone- or ligand-activated receptors associate with specific DNA sequences, or hormone response elements, in the regulatory regions of target genes. Transactivation alters the rate of transcription or induces the transcription of a particular gene(s). It refers to an increase in the rate and/or amount of transcription taking place.

The terms "transrepress," "transrepression" or "transrepressing" as used herein refer to the negative effects on regulation of gene transcription due to the interaction of a hormone or ligand with a receptor inducing a cascade of molecular events that ultimately lead to the specific association of the activated receptor with other transcription factors such as $NF_K$-B or AP-1. Transrepression can occur from the interaction of non-natural as well as natural ligands. Antagonist and agonist compounds which interact with steroid hormone receptor can cause transrepression. Once the ligand binds to the receptor, a conformational change occurs. Transrepression can occur via two different mechanisms, i.e., through the dimeric and monomeric form of the receptor. Use of the monomeric form of the receptor for transrepression depends on the presence of the DNA binding domain but not on the ability of the receptor to bind DNA. Use of the dimeric form of the receptor for transrepression depends on the receptor binding response elements overlapping cis-element(s). Transrepression alters the rate of transcription or inhibits the transcription of a particular gene. Transrepression decreases the rate and/or the amount of transcription taking place.

The term "progesterone receptor" as used herein also refers to a steroid hormone receptor which responds to or is activated by the hormone progesterone. Progesterone is part of the steroid hormone receptor superfamily as described above. The progesterone receptor can exist as two distinct but related forms that are derived from the same gene. The process for generation of the products may be alternate initiation of transcription, splicing differences, or transcription termination. These receptors are composed of DNA binding, ligand binding, as well as transregulatory domains. The progesterone receptor is also a ligand-dependent transcription factor capable of regulating gene expression. Interaction of the progesterone receptor with a ligand induces a cascade of molecular events that ultimately lead to the specific association of the activated receptor with regulatory elements of target genes.

The term "modified," modification," "mutant" or "mutated" refers to an alteration of the receptor from its naturally occurring wild-type form. This includes alteration of the primary sequence of a receptor such that it differs from the wild-type or naturally-occurring sequence. The mutant steroid hormone receptor protein as used in the present invention can be a mutant of any member of the steroid hormone receptor superfamily. For example, a steroid receptor can be mutated by deletion of amino acids on the carboxyl terminal end of the protein. Generally, a deletion of from about 1 to about 120 amino acids from the carboxyl terminal end of the protein provides a mutant steroid hormone receptor useful in the present invention. A person having ordinary skill in this art will recognize, however, that a shorter deletion of carboxyl terminal amino acids will be necessary to create useful mutants of certain steroid hormone receptor proteins. Other mutations or deletions can be made in other domains of the steroid receptor of interest, such as the DNA binding domain or the transregulatory domain.

For example, a mutant of the progesterone receptor protein will contain a carboxyl terminal amino acid deletion of approximately 1 to 60 amino acids. In a preferred embodiment of the present invention, 42 carboxyl terminal amino acids are deleted from the progesterone receptor protein. Likewise, a mutation of one or more amino acids in the DNA binding domain or the transregulatory domains can change the regulation of gene expression.

One skilled in the art will recognize that a combination of mutations and/or deletions are possible to gain the desired response. This would include double point mutations to the same or different domains. In addition, mutation also includes "null mutations" which are genetic lesions to a gene locus that totally inactivate the gene product.

One example is the generation of GR constructs by incorporating mutations in the GR to produce the desired effect. This would include, but is not limited to, mutations to amino acids 421 to 481 of the rat GR to eliminate the ability of the GR to transrepress promoter constructs dependent on AP-1 and $NF_K$-B while still retaining the ability to transactivate the expression of GRE-dependent promoter constructs. Such mutations which generate transactivation but not transrepressing activity include 1) the serine at position 425 changed to a glycine, the leucine at position 436 changed to a valine and the tyrosine and asparagine at positions 478 and 479 would be changed to leucine and glycine respectively. This is only an example and not a limitation. One skilled in the art will be well aware that other mutations can be created to provide the desired effect. Such mutations can be used in human GR constructs.

Mutations can also be generated in the D-loop of the DNA binding domain of GR that interfere with dimerization of GR. These mutations eliminate the ability of GR to transactivate but still promote transrepressing efficiently. In the case of rat GR such mutations transrepress even better than the wild type rat GR. Such mutations eliciting transrepression but not transactivation activity include the alanine at position 458 changed to a threonine, the asparagine and alanine at positions 454 and 458 changed to aspartic acid and threonine, respectively, and arginine and aspartic acid at positions 460 and 462 changed to aspartic acid and cysteine, respectively. The above mutated regions can be further and more precisely defined in humans by routine methodology, e.g., deletion or mutation analysis or their equivalent to obtain a ligand binding domain without natural ligand activity but with non-natural ligand activity. The above is only an example and meant to be non-limiting.

The term mutation also includes any other derivatives. The term "derivative" as used herein refers to a peptide or compound produced or modified from another peptide or compound of a similar structure. This could be produced in one or more steps. The term "modified" or "modification" as used herein refers to a change in the composition or structure of the compound or molecule. However, the activity of the derivative, modified compound, or molecule is retained, enhanced, or increased relative to the activity of the parent compound or molecule. This would include the change of one amino acid in the sequence of the peptide or the introduction of one or more non-naturally occurring amino acids or other compounds. This includes a change in a chemical body, a change in a hydrogen placement, or any type of chemical variation. In addition, "analog" as used herein refers to a compound that resembles another structure. Analog is not necessarily an isomer. The above are only examples and are not limiting.

The term "nucleic acid sequence," "gene," "nucleic acid" or "nucleic acid cassette" as used herein refers to the genetic material of interest which can express a protein, or a peptide, or RNA after it is incorporated transiently, permanently, or episomally into a cell. The nucleic acid can be positionally and sequentially oriented in a vector with other necessary elements such that the nucleic acid can be transcribed and, when necessary, translated into protein in the cells.

The term "genetic material" as used herein refers to contiguous fragments of DNA or RNA. The genetic material which is introduced into targeted cells can be any DNA or RNA. For example, the nucleic acid can be: (1) normally found in the targeted cells, (2) normally found in targeted cells but not expressed at physiologically appropriate levels in targeted cells, (3) normally found in targeted cells but not expressed at optimal levels in certain pathological conditions, (4) not normally found in the targeted cells, (5) novel fragments of genes normally expressed or not expressed in targeted cells, (6) synthetic modifications of genes expressed or not expressed within targeted cells, (7) any other DNA which may be modified for expression in targeted cells and (8) any combination of the above.

The term "gene expression" or "nucleic acid expression" as used herein refers to the gene product of the genetic material from the transcription and translation process. Expression includes the polypeptide chain translated from an mRNA molecule which is transcribed from a gene. If the RNA transcript is not translated, e.g., rRNA, tRNA, the RNA molecule represents the gene product.

The expression of the glucocorticoid-progesterone fusion protein receptor can be expressed as a cell surface, cytoplasmic or nuclear protein. By "cell surface protein" it is meant that a protein is wholly or partially spanning the cell membrane when expressed and which also is exposed on the surface of the cell. By cytoplasmic protein it is meant that a protein is contained completely within the cytoplasm, and does not span the nucleus or cell surfaces. As for "nuclear protein" it is meant that the protein is wholly or partially spanning the nuclear membrane when expressed and is exposed to the cell cytoplasm, or may be contained completely within the cell nucleus, not attached to the nuclear membrane and not exposed to cell cytoplasm.

A second aspect of the present invention features a modified glucocorticoid receptor protein. The glucocorticoid receptor protein contains a DNA binding domain, transregulatory domains and a mutated ligand binding domain. The modified protein is capable of binding a non-natural ligand by the mutated ligand binding domain. The mutated ligand domain is created by deleting about 2–5 carboxyl terminal amino acids from the ligand binding domain. In a preferred embodiment, the modified glucocorticoid receptor protein can be mutated by deleting amino acids 762 and 763, and substituting or altering amino acids 752 and 753, of the ligand binding domain. Substituted amino acids 752 and 753 can be changed to be both alanines.

A third aspect of the present invention features a modified glucocorticoid receptor protein. This protein contains a DNA binding domain and transregulatory domains. The transregulatory domains are capable of constitutively transactivating or transrepressing gene expression. The receptor protein is mutated by removing the ligand binding domain. As used herein the term "constitutively" refers to the ability to continually activate or repress gene expression without the need for a ligand.

A fourth aspect of the present invention features a modified glucocorticoid receptor protein. This protein is capable of binding a non-natural ligand. The modified receptor contains a glucocorticoid receptor region which comprises a DNA binding domain, a mutated transregulatory domain and a mutated ligand binding domain. The mutated transregulatory domains are capable of transactivating gene expression but not transrepressing gene expression.

For example, the mutated ligand binding domain is mutated as described above. The rat GR mutated transregulatory domain is mutated by changing the serine at position 425 to glycine, the leucine at position 436 to valine, and the tyrosine and asparagine at positions 478 and 479 to leucine and glycine. Such mutations can be used in human GR.

A fifth aspect of the present invention features a modified glucocorticoid receptor protein which is capable of binding a non-natural ligand. The modified receptor contain a glucocorticoid receptor region which comprises a mutated DNA binding domain, transregulatory domains and a mutated ligand binding domain. The mutated DNA binding domain prevents transactivation since DNA binding is necessary for such activation. The transregulatory domains are capable of transrepressing gene expression but not transactivating gene repression. Such activity occurs upon binding of the mutated binding ligand with the non-natural ligand.

For example, the mutated ligand binding domain is mutated as described above. The rat GR mutated DNA binding domain is mutated by changing the alanine at position 458 to threonine, the asparagine and alanine at positions 454 and 458 changed to aspartic acid and threonine respectively, and the arginine and aspartic acid at positions 460 and 562 changed to aspartic acid and cysteine, respectively. Such mutations can be used in human GR.

A sixth related aspect of the invention features a nucleic acid sequence encoding one of the modified glucocorticoid receptors as discussed above, including the fusion protein receptor. The nucleic acid is the genetic material which can express a protein, or a peptide, or RNA after it is incorporated transiently, permanently or episomally into a cell.

A seventh related aspect of the present invention features a vector containing a nucleic acid sequence for the modified glucocorticoid receptors discussed above. The vectors are capable of expressing the nucleic acid transiently, permanently or episomally into a cell or tissue. In one example, the vector is a plasmid designated as pGR0403R for the constitutively active GR and pGR0385 for mutated rat GR.

The term "vector" as used herein refers to a construction comprised of genetic material designed to direct transformation of a targeted cell. A vector contains multiple genetic elements positionally and sequentially oriented with other necessary elements such that the nucleic acid in a nucleic acid cassette can be transcribed and when necessary translated in the transfected cells. The term vector as used herein can refer to nucleic acid, e.g., DNA derived from a plasmid, cosmid, phagemid or bacteriophage, into which one or more fragments of nucleic acid may be inserted or cloned which encode for particular proteins. The term "plasmid" as used herein refers to a construction comprised of extrachromosomal genetic material, usually of a circular duplex of DNA which can replicate independently of chromosomal DNA. The plasmid does not necessarily replicate.

The vector can contain one or more unique restriction sites, and may be capable of autonomous replication in a defined host or organism such that the cloned sequence is reproduced. The vector molecule can confer some well-defined phenotype on the host organism which is either selectable or readily detected. The vector may have a linear or circular configuration. The components of a vector can contain but is not limited to a DNA molecule incorporating: (1) DNA; (2) a sequence encoding a therapeutic or desired product; and (3) regulatory elements for transcription, translation, RNA processing, RNA stability, and replication.

The purpose of the vector is to provide expression of a nucleic acid sequence in cells or tissue. Expression includes the efficient transcription of an inserted gene or nucleic acid sequence. Expression products may be proteins, polypeptides, or RNA. The nucleic acid sequence can be contained in a nucleic acid cassette. Expression of the nucleic acid can be continuous, constitutive, or regulated. The vector can also be used as a prokaryotic element for replication of plasmid in bacteria and selection for maintenance of plasmid in bacteria.

In the present invention the preferred vector comprises the following elements linked sequentially at an appropriate distance to allow functional expression: a promoter, a 5' mRNA leader sequence, a translation initiation site, a nucleic acid cassette containing the sequence to be expressed, a 3' mRNA untranslated region, and a polyadenylation signal sequence. As used herein the term "expression vector" refers to a DNA vector that contains all of the information necessary to produce a recombinant protein in a heterologous cell.

In addition, the term "vector" as used herein can also include viral vectors. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a vector of the present invention, that portion does not cause incorporation of the vector into a viral particle and thus is unable to produce an infective viral particle.

A vector as used herein can also include DNA sequence elements which enable extra-chromosomal (episomal) replication of the DNA. Vectors capable of episomal replication are maintained as extra-chromosomal molecules and can replicate. These vectors are not eliminated by simple degradation but continue to be copied. These elements may be derived from a viral or mammalian genome. These provide prolonged or "persistent" expression as described below.

The term "persistent expression" as used herein refers to introduction of genes into the cell together with genetic elements which enable episomal (i.e., extrachromosomal) replication. This can lead to apparently stable transformation of the cell without the integration of the novel genetic material into the chromosome of the host cell.

"Stable expression" as used herein relates to the integration of genetic material into chromosomes of the targeted cell where it becomes a permanent component of the genetic material in that cell. Gene expression after stable integration can permanently alter the characteristics of the cell and its progeny arising by replication leading to stable transformation.

An eighth related aspect of the present invention features a transfected cell containing a vector which contains nucleic acid sequence for a modified glucocorticoid receptor as discussed above. As used herein the term "transfected" or "transfection" refers to the incorporation of foreign DNA into any cells by exposing them to such DNA. This would include the introduction of DNA by various delivery methods, e.g., via vectors or plasmids.

Methods of transfection may include microinjection, $CaPO_4$ precipitation, liposome fusion (e.g., lipofection), electroporation or use of a gene gun. Those are only examples and are meant not to be limiting. The term "transfection" as used herein refers to the process of introducing DNA (e.g., DNA expression vector) into a cell. Following entry into the cell, the transfected DNA may: (1) recombine with the genome of the host; (2) replicate independently as an episome; or (3) be maintained as an episome without replication prior to elimination. Cells may be naturally able to uptake DNA. Particular cells which are not naturally able to take up DNA require various treatments, as described above, in order to induce the transfer of DNA across the cell membrane.

A ninth related aspect of the present invention features a transformed cell with a vector containing a nucleic acid sequence for a modified glucocorticoid receptor as discussed above. As used here in the term "transformed" or "transformation" refers to transient, stable or permanent changes in the characteristics (expressed phenotype) of a cell by the mechanism of gene transfer. Genetic material is introduced into a cell in a form where it expresses a specific gene product or alters the expression or effects of endogenous gene products.

The term "stable" as used herein refers to the introduction of gene(s) into the chromosome of the targeted cell where it integrates and becomes a permanent component of the genetic material in that cell. Gene expression after stable transformation can permanently alter the characteristics of the cell leading to stable transformation. An episomal transformation is a variant of stable transformation in which the introduced gene is not incorporated in the host cell chromosomes but rather is replicated as an extrachromosomal element. This can lead to apparently stable transformation of the characteristics of a cell. "Transiently" as used herein refers to the introduction of a gene into a cell to express the nucleic acid, e.g., the cell express specific proteins, peptides or RNA, etc. The introduced gene is not integrated into the host cell genome and is accordingly eliminated from the cell over a period of time. Transient expression relates to the expression of a gene product during a period of transient transfection. Transient expression also refers to transfected cells with a limited life span.

Transformation can be performed by in vivo techniques as described below or ex vivo techniques in which cells are co-transfected with a vector containing a selectable marker. This selectable marker is used to select those cells which have become transformed. It is well known to those skilled in the art the type of selectable markers to be used with transformation studies. Transformation can be tissue specific to regulate expression of the nucleic acid predominantly in the tissue or cell of choice.

Transformation of the cell may be associated with production of a variety of gene products including protein and RNA. These products may function as intracellular or extracellular structural elements, ligands, hormones, neurotransmitters, growth regulating factors, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity. Other examples can be found above in the discussion of nucleic acid cassette. The product expressed by the transformed cell depends on the nucleic acid of the nucleic acid cassette. This list is only an example and is not meant to be limiting. In the present invention the nucleic acid to be expressed is a fusion protein as referenced above, or variations thereof or any of the other receptor proteins disclosed herein.

In one embodiment the transformed cell is a muscle cell. The term "muscle" refers to myogenic cells including myoblasts, skeletal, heart and smooth muscle cells. The muscle cells or tissue can be in vivo, in vitro or tissue culture and capable of differentiating into muscle tissue. In another embodiment, the transformed cell is a lung cell. The term "lung cell" as used herein refers to cells associated with the pulmonary system. The lung cell can also be in vivo, in vitro or tissue culture.

In still another embodiment, the transformed cell is a cell associated with the joints. The term "cells associated with the joints" refers to all of the cellular and non-cellular materials which comprise the joint (e.g., knee or elbow) and are involved in the normal function of the joint or are present within the joint due to pathological conditions. These include material associated with: the joint capsule such as synovial membranes, synovial fluid, synovial cells (including type A cells and type B synovial cells); the cartilaginous components of the joint such as chondrocyte, extracellular matrix of cartilage; the bony structures such as bone, periosteum of bone, periosteal cells, osteoblast, osteoclast; the immunological components such as inflammatory cells, lymphocytes, mast cells, monocytes, eosinophil; other cells like fibroblasts; and combinations of the above. Once transformed these cells express the fusion protein. One skilled in the art will quickly realize that any cell is capable of undergoing transformation and within the scope of this invention.

A tenth aspect of the present invention features methods for transforming a cell with a vector containing nucleic acid encoding for a modified glucocorticoid receptor. This method includes the steps of transforming a cell in situ by contacting the cell with the vector for a sufficient amount of time to transform the cell. As discussed above, transformation can be in vivo or ex vivo. Once transformed the cell expresses the mutated glucocorticoid receptor. This method includes methods of introducing and methods of incorporating the vector. "Incorporating" and "introducing" as used herein refer to uptake or transfer of the vector into a cell such that the vector can express the therapeutic gene product within a cell as discussed with transformation above.

An eleventh aspect of the present invention features a method of using the modified glucocorticoid receptors discussed above. This method comprises the steps of transforming a cell with a vector containing a nucleic acid encoding for the modified glucocorticoid receptor of interest. The transformed cells are able to express the mutated glucocorticoid receptor. The receptor is capable of regulating by a non-natural ligand the expression of glucocorticoid responsive genes, whether such regulation is transactivation or transrepression. The term "glucocorticoid responsive genes" as used herein refers to genes whose expression is regulated by the activation of the glucocorticoid receptor. Such regulation includes both positive and negative regulation of gene expression. This also includes GRE (glucocorticoid response element) controlled genes.

This method of use includes methods of gene replacement using the fusion protein, methods of gene therapy using the fusion protein and methods of administering the fusion protein in which the same steps are used. "Gene replacement" as used herein means supplying a nucleic acid sequence which is capable of being expressive in viva in an animal and thereby providing or augmenting the function of an endogenous gene which is missing or defective in the animal.

The methods of use also include methods for using the modified glucocorticoid receptor to activate GRE controlled genes. Such genes can be co-transfected with the modified glucocorticoid receptors. Such co-transfection allows activated expression of the GRE controlled genes. Furthermore, the methods of use include the use of tissue specific delivery systems, and use of mRNA stability constructs.

The present invention features methods for administration as discussed above. Such methods include methods for administering a supply of polypeptide, protein or RNA to a human, animal or to tissue culture or cells. These methods of use of the above-referenced vectors comprises the steps of administering an effective amount of the vectors to a human, animal or tissue culture. The term "administering" or "administration" as used herein refers to the route of introduction of a vector or carrier of DNA into the body. The vectors of the above methods and the methods discussed below may be administered by various routes. Administration may be intravenous, intratissue injection, topical, oral, or by gene gun or hypospray instrumentation. Administration can be directly to a target tissue, e.g. direct injection into synovial cavity or cells, or through systemic delivery. These are only examples and are nonlimiting.

Administration will include a variety of methods, such as direct gene transfer into muscle tissue by liposomes, proteoliposomes, calcium phosphate-co-precipitated DNA, DNA coupled to macro-molecular complexes, DNA transporters, DNA coated to micro-projectiles, coated plasmids, direct micro-injection, as well as tissue grafting. Direct gene transfer of vectors can be administered by microinjection, electroporation, liposomes, proteoliposomes, calcium-phosphate-co-precipitation, tissue grafting, retroviral vectors, DNA coupled to macromolecular complexes, DNA transporters, gene gun and micro-projectiles. See, e.g., WO 93/18759, hereby incorporated by reference herein. The preferred embodiment is by direct injection. Routes of administration include intramuscular, aerosol, oral, topical, systemic, ocular, intraperitoneal, intrathecal and/or fluid spaces.

The term "effective amount" as used herein refers to sufficient vector administered to humans, animals or into tissue culture cells to produce the adequate levels of polypeptide, protein, or RNA. One skilled in the art recognizes that the adequate level of protein polypeptide or RNA will depend on the intended use of the particular vector. These levels will be different depending on the type of administration, treatment or vaccination as well as intended use.

In one embodiment of the present invention, the method of using the mutated glucocorticoid receptors discussed above uses RU486 as the non-natural ligand to regulate gene expression. This ligand is capable of binding the mutated progesterone or glucocorticoid ligand binding domain and activating the transregulatory domains of the receptor. RU486 is capable of activating or repressing the appropriate glucocorticoid responsive genes. This is only and example and not meant to be limiting. Those skilled in the art will recognize that other non-natural ligands can be used.

The method of use can regulate transactivation of glucocorticoid responsive genes or GRE controlled genes or gene constructs. In addition, the method of use can regulate transrepression of glucocorticoid responsive genes such as metalloproteinases, interleukins, cyclooxygenases, and cytokines. Although such genes respond to other stimuli, these genes are repressed by steroids. Typically, without the primary stimulant, steroids have little effect on the basal transcription of such genes. Genes such as IL-2, IL-6, IL-8, ICAM-1, VCAM-1 have been repressed by steroids. Any gene transcription depending on AP-1 or $NF_K$-B will be repressed in the present invention.

A twelfth aspect of the present invention features a method for treating arthritis. This method includes the transformation of cells associated with the joints with the above referenced vectors. The vectors contain nucleic acid which encode for the modified glucocorticoid receptor protein. Once expressed in the cells associated with the joints, the mutated protein is capable of transactivating or transrepressing by a non-natural ligand the expression of glucocorticoid responsive genes or GRE controlled genes, including transfected GRE controlled gene constructs.

With respect to the joints, diseases which can be treated by the methods of the present invention include those diseases known to one in the art as arthritis. This includes pathophysiological conditions resulting from inflammatory processes; hypertrophy or inappropriate proliferation of cellular elements of the joint; damage to the joint; enhancement of repair, regeneration, and recovery of essential structures comprising the joint after surgery or injury; and other acquired diseases of the joints. For example, in the treatment of a pathological condition the vector with or without a formulation will be introduced into cells comprising structures of the joint by injecting a pharmacological dose of the vector with or without a formulation into a joint. The nucleic acid cassette in the vector encodes a protein, polypeptide or RNA. The vector is taken up by appropriate cells within the joint and expresses the protein, polypeptide or RNA. The preferred embodiment of this invention involves transient or persistent expression within the joint. This is preferable to stable expression since it enables adjustment of the level of expression in response to the evolution of the disease process.

Specific diseases which can be treated by administration of vectors to cells within the joint include various arthritises, avascular necrosis, or injuries requiring repair and regeneration of structures comprising the joint. The various types of arthritis which can be treated, include but are not limited to: tendinitis; bursitis; fibrositis; bone lesions; soft tissue inflammation; degenerative joint disease; traumatic disorders; neuropathic arthropathy; metabolic disorders; synovial tumors; pigmented villonodular synovitis; hemorrhagic disorders; septic disorders; crystal-induced disorders (gout); immune complex disease and vasculitis; systemic lupus erythematosus; rheumatoid arthritis; Reiter's syndrome; psoriasis; ankylosing spondylitis; scleroderma; and arthritis of intestinal disease. In a specific embodiment of the present invention, an anti-inflammatory cytokine may be expressed including IL-4, IL-10, or TGF-β.

Cells associated with fluid spaces incorporate the formulated DNA expression vector into the cell. "Incorporate" refers to uptake or transfer of the formulated DNA expression vector into a cell such that the formulated DNA expression vector can express the therapeutic gene product within the cell, i.e., the mutated receptor. Significantly, incorporation may involve, but does not require, integration of the DNA expression vector or episomal replication of the DNA expression vector. Incorporation in this sense includes the short term persistence of the DNA expression vector in the cell before it is eliminated by degradation or translocation to other compartments.

Incorporation includes expression of the nucleic acid cassette by cells, whether it is transient expression, persistent expression, or stable expression. "Transient expression" as used herein relates to the introduction of genetic material into a cell to express specific proteins, peptides or RNA, etc. The introduced genetic material is not integrated into or replicated by the host cell genome, but is accordingly eliminated from the cell over a period of time by degradation or translocation to other compartments. These terms are defined in more detail above.

A thirteenth aspect of the present invention features a method for treating asthma. This method includes the transformation of cells associated with the lungs or pulmonary system with the above referenced vectors. The vectors contain nucleic acid which encodes the fusion protein. Once expressed in the lung cells the mutated receptor is capable of transactivating or transrepressing the expression by a non-natural ligand of the appropriate glucocorticoid responsive genes and/or GRE controlled transgenes.

In one embodiment, the above methods of treatment invoke use of RU486 as the non-natural ligand. The transactivation and transrepression can occur when the mutated glucocorticoid receptor is activated by RU486. The genes that are transrepressed or transactivated in response to ligand binding to the fusion protein are described above.

A fourteenth aspect of the present invention features a transgenic animal whose cells contain the vectors of the present invention. These cells include germ or somatic cells. Transgenic animal models can be used for understanding of molecular carcinogenesis and disease, assessing and exploring novel therapeutic avenues for effects by potential chemical and physical carcinogens and tumor promoters.

An additional preferred embodiment provides for a transgenic animal containing a modified glucocorticoid receptor vector. By "transgenic animal" is meant an animal whose genome contains an additional copy or copies of the gene from the same species or it contains the gene or genes of another species, such as a gene encoding for a mutated glucocorticoid receptor introduced by genetic manipulation or cloning techniques, as described herein and as known in the art. The transgenic animal can include the resulting animal in which the vector has been inserted into the embryo from which the animal developed or any progeny of that animal. The term "progeny" as used herein includes direct progeny of the transgenic animal as well as any progeny of succeeding progeny. Thus, one skilled in the art will readily recognize that if two different transgenic animals have been made each utilizing a different gene or genes and they are mated, the possibility exists that some of the resulting progeny will contain two or more introduced genes. One skilled in the art will readily recognize that by controlling the matings, transgenic animals containing multiple introduced genes can be made.

BRIEF DESCRIPTION OF THE DRAWINGS

FIGS. 2A–B illustrates the functional and structural characterization of the UP-1 mutant. FIG. 2B shows partial nucleotide sequences, identified as SEQ. ID. NO. 2 and SEQ. ID. NO. 3, for wild-type progesterone receptor and the mutant UP-1 receptor, respectively. FIG. 2B also shows partial amino acid sequences, identified as SEQ. ID. NO. 4 and SEQ. ID. NO. 5, for wild-type progesterone receptor and the mutant UP-1 receptor, respectively.

FIG. 4 shows the transcriptional activity and hormone binding analysis of wild type and mutant human progesterone receptor constructs.

FIG. 7 depicts the GR-PR fusion constructs.

FIG. 8 depicts the Rat and Human GR double point mutation constructs.

FIGS. 9A–B illustrates the nucleic acid sequence encoding a plasmid pGR0403R (SEQ. ID. NO. 1) expressing a constitutively active mutant GR protein.

The drawings are not necessarily to scale. Certain features of the invention may be exaggerated in scale or shown in schematic form in the interest of clarity and conciseness.

DETAILED DESCRIPTION OF THE INVENTION

The following are examples of the present invention using the mutated steroid receptors for gene therapy. It will be readily apparent to one skilled in the art that various substitutions and modifications may be made to the invention disclosed herein without departing from the scope and spirit of the invention. Thus, these examples are offered by way of illustration and are not intended to limit the invention in any manner.

The following are specific examples of preferred embodiments of the present invention. These examples demonstrate how the molecular switch mechanisms of the present invention can be used in construction of various cellular or animal models and how such molecular switch mechanisms can be used to transactivate or transrepress the regulation of gene expression. The utility of the molecular switch molecules is noted herein and is amplified upon in co-pending application by Vegeto, et al., entitled "Mutated Steroid Hormone Receptors, Methods for Their Use and Molecular Switch for Gene Therapy," supra and related U.S. Patent by Vegeto, et al., entitled " Progesterone Receptor Having C-Terminal Hormone Binding Domain Truncations," supra. Such sections (including drawings) are hereby specifically incorporated by reference herein.

Mutacenesis and Characterization of the Ligand Binding Domain of Human Progesterone Receptor Yeast Strain The *Saccharomyces cerevisiae* strain BJ3505 (MATAα, pep4:HIS3, prb1-Δ1.6R, his3Δ200, lys2-801, trpl-Δ101, ura3-52, gal2, (CUPl)) was used (Yeast Genetic Stock Center, Berkeley, Calif.). All yeast transformations were carried out following the lithium acetate transformation protocol (Ito, et al., *J. Bacteriol.* 153:163–168, 1983).

The PCR reactions were carried out using YEphPR-B DNA template (a YEp52AGSA-derived yeast expression plasmid containing the cDNA of hPR form-B (Misrahi, et al., *Biochem. Bioph. Res. Comm.* 143:740–748, 1987) inserted downstream of the yeast methallothionein-CUP1 promoter) and using three different sets of primers. In order to decrease the fidelity of the second strand polymerization reaction, buffer conditions of 1.5 mM $MgCl_2$, 0.1 mM dNTPs and pH 8.2 were used. About 2000 primary transformants were obtained from each region-specific library.

Yeast Mutant Screening

Figure 1:
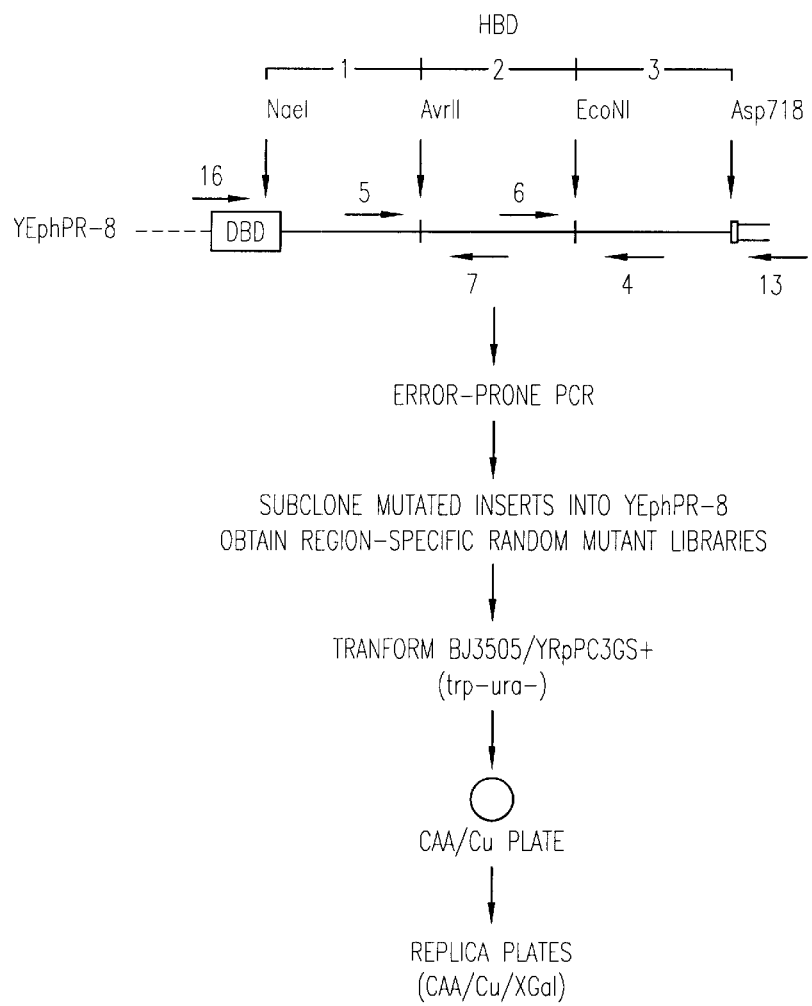
FIG. 1 shows the mutagenesis and screening strategy used in the present experiments.

Colonies of each library of hPR molecules mutated in specific subregions were pooled, large amounts of DNA were prepared and used to transform yeast cells carrying the reporter plasmid YRpPC3GS+, which contains two GRE/PRE elements upstream of the CYC1 promoter linked to the Lac-Z gene of *E. coli* (Mak, et al., *J. Biol. Chem.* 265:20085–20086, 1989). The transformed cells were plated on 1.5% agar plates containing 2% glucose, 0.5% casamino acids (5% stock solution of casamino acids is always autoclaved before use to destroy tryptophan), 6.7 g/l yeast nitrogen base (without amino acids) and 100 μM CuSO4 (CAA/Cu plates) and grown for 2 days at 30° C. These colonies were then replica-plated on CAA/Cu plates containing 0.16 g/l of 5-bromo-4-chloro-3-indolyl-β-D-galactoside (X-Gal, an indicator of β-galactosidase activity) with or without the hormones as indicated in FIG. 1 and allowed to grow for one day at 30° C. then two days at room temperature in the dark.

Growth of Yeast Culture for In Vitro Assay

Saccharomyces cerevisiae cells containing YEphPRB and the reporter plasmid were grown overnight at 30° C. in minimal media containing 2% glucose. The cells were subcultured in fresh medium and allowed to grow until early mid-log phase ($O.D._{600nm}=1.0$). Induction of receptor was initiated by the addition of 100 μM copper sulfate to the culture. Cells were harvested by centrifugation at 1,500 ×g for 10 minutes and resuspended in the appropriate buffer. This and all subsequent steps of analysis of the yeast extracts were done at 4° C.

Transcription Assay

Yeast cells containing the reporter and expression plasmids were grown overnight as described above in Example 3 in the presence of 100 μM copper sulfate. When the cell density reached $O.D._{600nm}=1.0$, hormones were added to the cultures. After a 4 hour incubation, yeast extracts were prepared and assayed for β-galactosidase activity as described previously (Miller, J. M. Miller ed., 352–355, 1972).

Generally, reporters useful in the present invention are any which allow for appropriate measurement of transcription levels. Preferable reporter systems include reporter vectors comprised of the yeast iso-l-cytochrome C proximal promoter element fused to a structural gene, wherein said structural gene is selected from the group consisting of β-galactosidase, galactokinase and URA3. More preferably, the vector is comprised of an insertion site for a receptor response element. The vectors which include β-galactokinase as an indicator of transcriptional activity are derived from the parent vector PC2 while the vectors which include galactokinase are derived from YCpR1 vector. Preferably, the structural genes originate from *E. coli*.

Western Immunoblotting

Yeast cells were grown as discussed above for the transcription assay. Yeast extracts for Western blot analysis were prepared by resuspending the cell pellet in TEDG+salts. The cell suspension was mixed with an equal volume of glass beads and disrupted by vortexing in a microcentrifuge tube. The homogenate was centrifuged at 12,000 ×g for 10 minutes. The supernatant was collected and the protein concentration was estimated using bovine serum albumin as standard. Yeast extracts were resolved on a 0.1% sodium dodecyl sulfate-7% polyacrylamide gel and transferred to Immobilon membrane as described previously (McDonnell, et al., *Mol. Cell. Biol.* 9:3517–3523, 1989). Solid phase radioimmunoassay was performed using a monoclonal antibody (JZB39) directed against the N-terminal domain of A and B forms of hPR.

Hormone Binding Competition Assays

Induction of PR synthesis was initiated by the addition of 100 μM $CuSO_4$ to the culture and incubation was continued for 6 hours. The cell pellet was resuspended in TESH buffer containing 1 μg/ml leupeptin, 10 μg/ml PMSF and 10 μg/ml pepstatin. The cell suspension was mixed with an equal volume of glass beads (0.5 mm; B. Braun Instruments) and disrupted by vortexing in a micro-centrifuge tube. The homogenate was centrifuged at 12,000 ×g for 10 minutes and the supernatant was further centrifuged at 100,000 ×g for 30 minutes to obtain a cytosol fraction. Diluted yeast extracts (200 μl) containing 100 μg of total protein were incubated overnight at 4° C. with [$^3$H] ligand in the absence (total binding) or presence (non-specific binding) of a 100-fold excess of unlabelled ligand. Bound and free steroids were separated by addition of 500 μl of dextran-coated charcoal suspension (0.5% Norit A, 0.050- dextran, 10 mM Tris HCl, pH 7.4 and 1 mM EDTA). Specific binding was determined by subtracting nonspecific from total binding. Scatchard analysis was carried out as described previously by Mak, et al., *J. Biol. Chem.* 264:21613:21618 (1989).

Site-directed Mutagenesis

Mutants YEPhPR-B879 and YEphPR-B891 were prepared following the procedure described by Dobson, et al., *J. Biol. Chem.* 264:4207–4211 (1989). CJ236 cells were infected with mpPR90 (an M13 plasmid containing hPR cDNA). The resulting uridine-containing single-stranded DNA was annealed to 20-mer oligonucleotides containing a TGA stop codon corresponding to amino acids 880 and 892, respectively.

Construction of Mammalian Expression Vectors

The mammalian expression vector phPR-B contains the SV40 enhancer sequence upstream of the human growth hormone promoter linked to the hPR-B cDNA. This vector was digested with Sal1 and EcoRl. The 6.1kb fragment (containing the vector sequences and the 5'-1.5 kb of the hPR) was gel-purified and ligated to the 2.1 kb fragment of YEphPR-B891 (containing the 3'-end of the receptor). previously cut with Sal1 and EcoRl. The resulting plasmid, phPR-B891, encodes a 42 amino acid truncated version of hPR form B.

Mammalian Cell Transient Transfections and CAT-Assays

Five μg of chloramphenicol acetyltransferase (CAT) reporter plasmid, containing two copies of a PRE/GRE from the tyrosine amino transferase gene linked to the thymidine kinase promoter (PRETKCAT), were used in transient cotransfection experiments together with 5 μg of wild type or mutant receptor DNAs. Transient cotransfections and CAT-assays were performed as described by Tsai, et al., *Cell* 57:443–448 (1989).

Mutagenesis of the Hormone Binding Domain of hPR-B

In order to characterize amino acids within the hPR HBD which are critical for ligand binding and hormone-dependent transactivation, libraries of mutated hPR molecules were created and the mutants introduced into a reconstituted progesterone-responsive transcription system in yeast. This system allowed the screening of large numbers of mutant clones and the direct, visual identification of phenotypes.

Unique restriction sites for NaeI, AvrII and EcoNI were created in the cDNA of hPR, obtaining three cassettes of 396, 209 and 400 nucleotides (regions 1, 2 and 3, respectively). For PCR mutagenesis three sets of primers (16 +7 for region 1, 5 +4 for region 2 and 6 +13 for region 3) were used in the polymerization reaction using YEphPR-B as DNA template. The fragments obtained after PCR were digested with the appropriate enzymes, gel-purified and ligated into the parental plasmid YEphPR-B. Ligation mixes were used to transform bacterial cells and to obtain libraries of hPR molecules randomly point-mutated in the HBD. 5 $\mu$g of DNA were used from each library to transform yeast cells carrying the reporter plasmid YRpPC3GS+and transformants were selected for tryptophan and uracil auxotrophy on CAA plates containing 100 $\mu$M $CuSO_4$. These were then replicated on CAA plates containing the hormones. The screening for "up-mutations" allowed identification of receptor mutants with hormone-independent transcriptional activity, or increased affinity for the ligand (these clones should remain blue when grown with 100-fold less hormone), or with an altered response to RU486 or a glucocorticoid analogue. In the "down-mutation" screening, receptor mutants that were transcriptionally inactive in the presence of the ligand were detected.

Because of the nature of the method used to generate the mutated DNA templates, it was necessary, firstly, to determine the quality of the libraries obtained. This was assessed by estimating the number of null-mutations generated by mutagenesis. We estimated the frequency of occurrence of transcriptionally inactive receptors (white colonies) compared to the total number of colonies. This frequency was about 70.

The primary transformants were replica-plated onto plates containing the antiprogestin RU486. The wild type receptor is not activated by this hormone (FIG. 1). Using this screening strategy, a single colony was identified that displayed considerable transcriptional activity in response to the antihormone. Interestingly, the same colony did not display transcriptional activity when replica-plated in the presence of progesterone. The colony was purified and the phenotype was confirmed. Eviction of the expression vector from the clone, followed by reintroduction of the unmutated receptor, demonstrated that the phenotype was indeed related to the expression vector and was not the result of a secondary mutation. In addition, the mutated plasmid called UP-1, was rescued from yeast by passage through *E.coli* (as described in Ward, *Nucl. Acids Res.* 18:5319 (1990) and purified. This DNA was then reintroduced into yeast that contained only the reporter plasmid. As expected, the mutant phenotype was stable and related directly to the receptor expression plasmid.

Characterization of the UP-1 Mutant

The plate assays used to identify the receptor mutants are qualitative in nature. To further characterize the properties of UP-1, the activity of the receptor mutants was compared with that of the wild type receptor in a transcription assay. In this method, yeast cells transformed with either the wild type or the mutant receptor and a progesterone responsive reporter were grown overnight in the presence of 100$\mu$M $CuSO_4$. When the cells had reached an $O.D._{600nm}$ of 1.0, they were supplemented with progesterone or RU486 and harvested by centrifugation after four hours. The $\beta$-galactosidase activity in the cell cytosol was then measured.

Figure 2A:
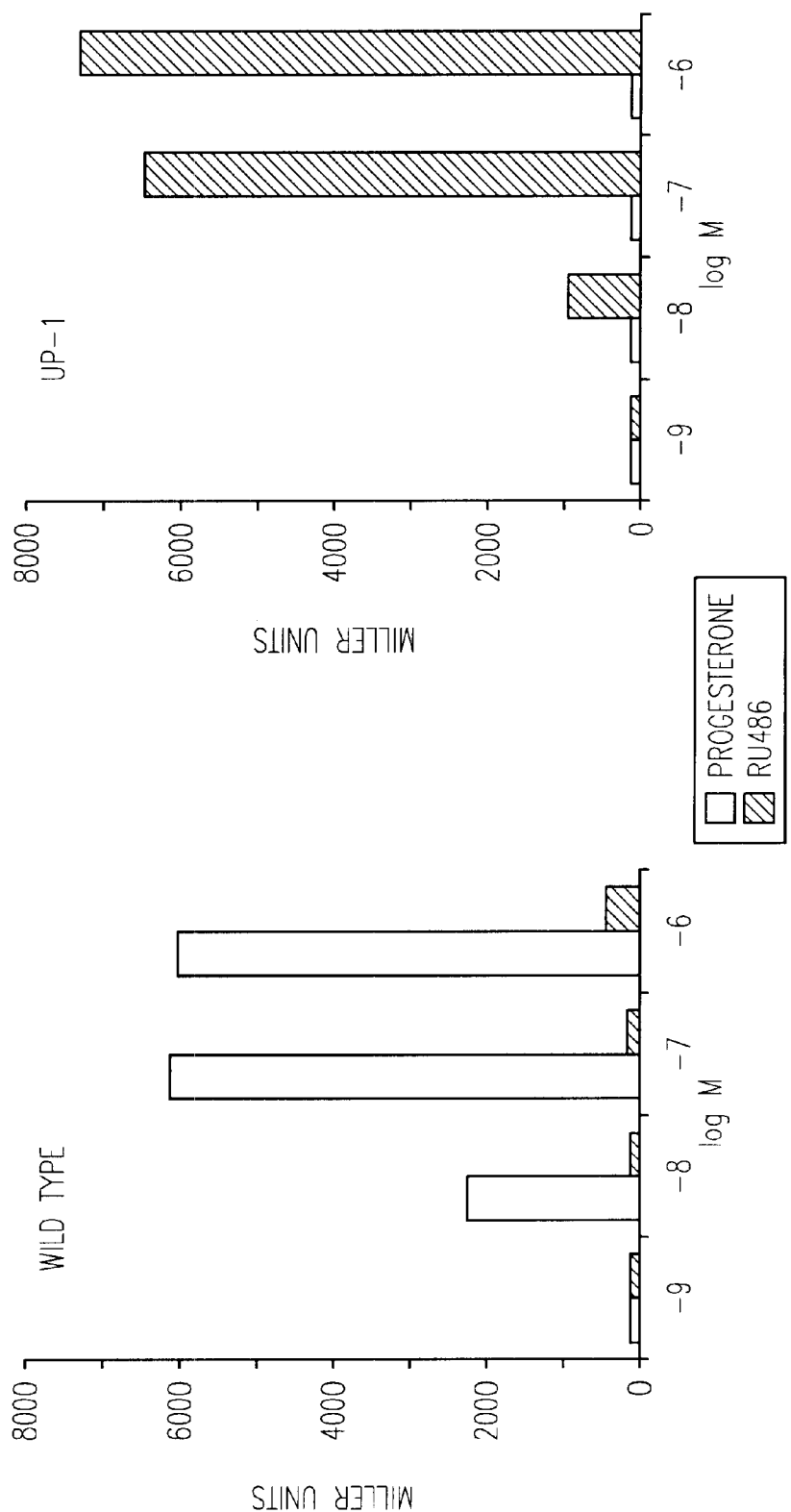

With reference to FIG. 2, panel (A), when assayed with the wild type receptor, 1 $\mu$M RU486 is a weak inducer of transcription, whereas progesterone caused a greater than 60-fold induction of transcription at 1 $\mu$M. However, this situation was reversed when the mutant was analyzed. In this case, RU486 was an extremely potent activator, whereas progesterone was ineffective. Interestingly, the activity achieved by the mutant in the presence of RU486 was of the same order of magnitude as that of the wild type assayed in the presence of progesterone. This reversal in specificity clearly indicates that the mechanism by which these ligands interact with the receptor is basically different.

FIG. 2 shows the DNA and amino acid sequences of the wild type and mutant DNAs (SEQ. ID. NOS. 2, 3, 4, and 5). The cytosine at position 2636 was missing in the mutant DNA, therefore, a shifted reading frame was created and a stop codon was generated 36 nucleotides downstream of the C-2636 deletion. A schematic structure of the wild type and UP-1 receptors is also presented with a depiction of the 12 C-terminal amino acids unique to the mutant receptor (SEQ. ID. NO. 5). Conserved and structurally similar amino acids are marked by an apostrophe and asterisk, respectively.

DNA sequence analysis of UP-1 identified a single nucleotide deletion at base 2636 (FIG. 2B). This mutation results in a shift of the reading frame which generates a stop codon 36 nucleotides downstream. As a result, the wild type receptor is truncated by 54 authentic amino acids and 12 novel amino acids are added at the C-terminus.

Western Analysis of the Mutant Human Progesterone Receptor

Figure 3:
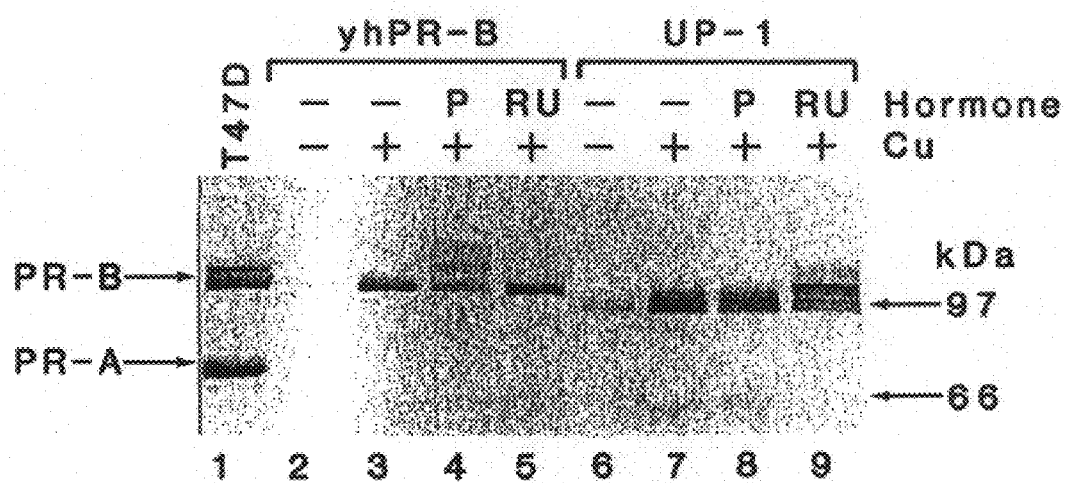
FIG. 3 shows a western analysis of the mutant human progesterone receptor.

FIG. 3 shows a western analysis of mutant hPR. Yeast cells carrying the reporter plasmid and wild type (yhPR-B or mutant (UP-1) hPR were grown overnight in CAA medium with (lanes 3 to 5 and 7 to 9) or without (lanes 2 and 6) 100 $\mu$M $CuSO_4$. 1 $\mu$M progesterone or 1 $\mu$M RU486 were added as indicated and cells were grown for another 4 hours. Yeast extracts were prepared as described above. 50 $\mu$g of protein extract were run on a 0.10 SDS-70 polyacrylamide gel. 50 $\mu$g of a T47D nuclear extract containing the A and B forms of hPR were also loaded (lane 1) as a positive control. The positions of molecular weight markers are indicated.

A Western immunoblot analysis of UP-1 and wild type receptors was performed in order to verify that the mutant receptor was synthesized as predicted from its DNA sequence and to eliminate the possibility that some major degradation products were responsible for the mutant phenotype. As shown in FIG. 3, the mutant receptor migrated faster in the gel, confirming the molecular weight predicted by DNA sequencing. The wild type receptor (yhPR-B) ran as a 114 kDa protein, while the mutant receptor was 5kDa smaller (compare lanes 2 and 3 with 6 and 7). The addition of 100 $\mu$/M $CuSO_4$ to the cell cultures increased synthesis of both the wild type and mutant hPR to the same extent. No major degradation products were detected. In the presence of progesterone and RU486, yhPR-B bands were upshifted due to hormone-induced phosphorylation of the receptor. In contrast, RU486 induced upshifting of wild type PR to a lesser extent (lanes 4 and 5). For the UP-1 mutant this hormone-dependent upshifting was seen upon treatment with RU486 (lanes 8 and 9). Thus, the C-terminus of PR may be responsible for the inactivity of RU486. Consequently, removal of this sequence would enable RU486 to become an agonist.

Hormone Binding Analysis

FIG. 4 shows the transcriptional activity and hormone binding analysis of wild type and mutant hPR constructs. hPR constructs are reported to the left side together with a schematic representation of the receptor molecules. Yeast cells were grown in the presence of 100 μM $CuSO_4$. Transcriptional analysis was done as described above. Experiments were done in triplicate and transcriptional activities were normalized with respect to protein. Hormone binding assays were performed in the presence of 20 nM [$^3$H] progesterone or 20 nM [$^3$H] RU486.

A saturation binding analysis of the UP-1 mutant receptor was performed in order to determine if its affinity for RU486 and progesterone was altered. Scatchard analysis of the binding data demonstrated that both the wild type and mutant receptors had a similar affinity for RU486 of 4 and 3 nM, respectively. As seen in FIG. 4, the mutant receptor molecule had lost the ability to bind progesterone. Thus, the amino acid contacts for progesterone and RU486 with hPR are different.

Generation of Deletion Mutants of hPR-B

As shown in FIG. 2B, DNA sequencing revealed that the frameshift mutation in the UP-1 clone created a double mutation in the receptor protein. That is, a modified C-terminal amino acid sequence and a 42 amino acid trunca-tion. In order to identify which mutation was ultimately responsible for the observed phenotype, two new receptor mutants were constructed in vitro: YEphPR-B879, containing a stop codon corresponding to amino acid 880, and YEphPRB891, containing a stop codon at amino acid 892. Hormone binding data (see FIG.4) demonstrated that both of these truncated receptors could bind RU486 but not progesterone. When examined in vivo, both mutant receptors activated transcription in the presence of RU486 to levels comparable to those of the mutant UP-1 generated in yeast. As expected, both mutants were inactive in the presence of progesterone. Thus, the observed phenotype was not due to second site mutations in the UP-1 molecule. Also, 12 additional amino acids, from 880 to 891, were not responsible for the mutant activity. In addition, it is clear the C-terminal 42 amino acids are required for progesterone to bind to the receptor while the last 54 amino acids are unnecessary for RU486 binding. Thus, the antagonist is contacting different amino acids in the native receptor molecule and may induce a distinct receptor conformation relative to agonists.

In addition to the above deletion mutations, other deletions in the C-terminal amino acid sequence have provided binding activity with RU486 and not with progesterone. Such deletions include: (1) a 16 amino acid deletion leaving amino acids 1–917 of the progesterone receptor; and (2) a 13 amino acid deletion leaving amino acids 1–920 of the progesterone receptor. Use of the receptor binding region with TATA-CAT expression in transient transfection assays showed CAT expression with the 16 amino acid deletion, i.e., amino acids 640–917, and the 13 amino acid deletion, i.e., amino acids 640–920.

Steroid Specificity for Activation of Transcription of the UP-1 Mutant

FIG. 5 shows the specificity of the transcriptional activity of the mutant hPR. In panel (A), wild type and UP-1 mutant receptor transcriptional activities were assayed in the presence of different concentrations of progesterone, RU486, Org31806 and Org31376 as indicated.

Figure 5A:
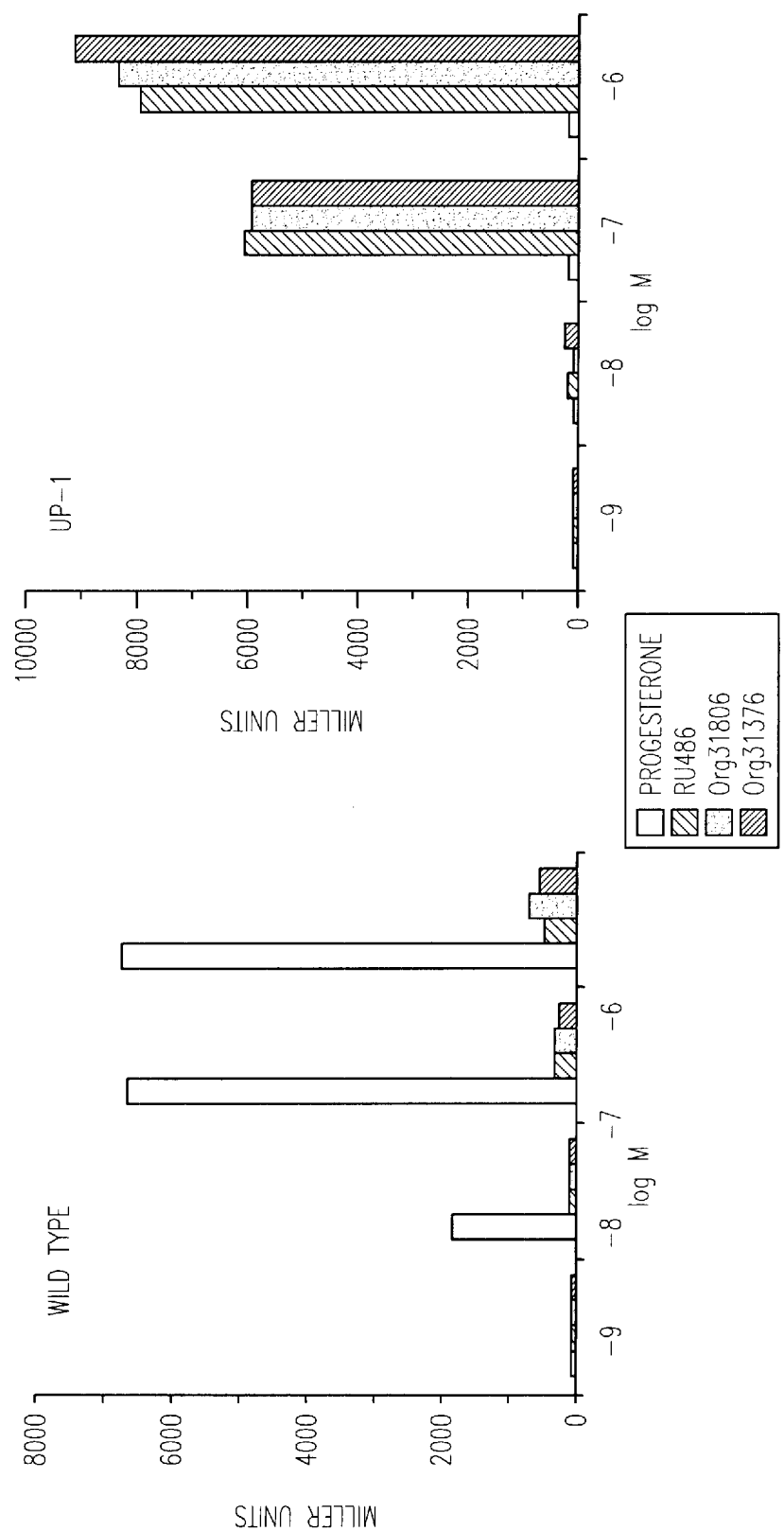
FIGS. 5A–B shows the specificity of transcriptional activity of the mutant human progesterone receptor.

A transcription assay was performed using two synthetic antagonists, Org31806 and Org31376, which are potent antiprogestins. As shown in FIG. 5A, the mutant receptor was activated by both of these compounds. The curve of the concentration-dependent activity was similar to that obtained with RU486, suggesting that the affinity of these two antagonists for the mutant receptor is similar to that of RU486. When assayed with the wild type receptor, these compounds had minimal transcriptional activity and behaved like partial agonists (3–10% of progesterone activity) only at concentrations of 1 μM, as does RU486. Thus, the inhibitory effect of the C-terminus of hPR extends to other receptor antagonists.

Figure 5B:
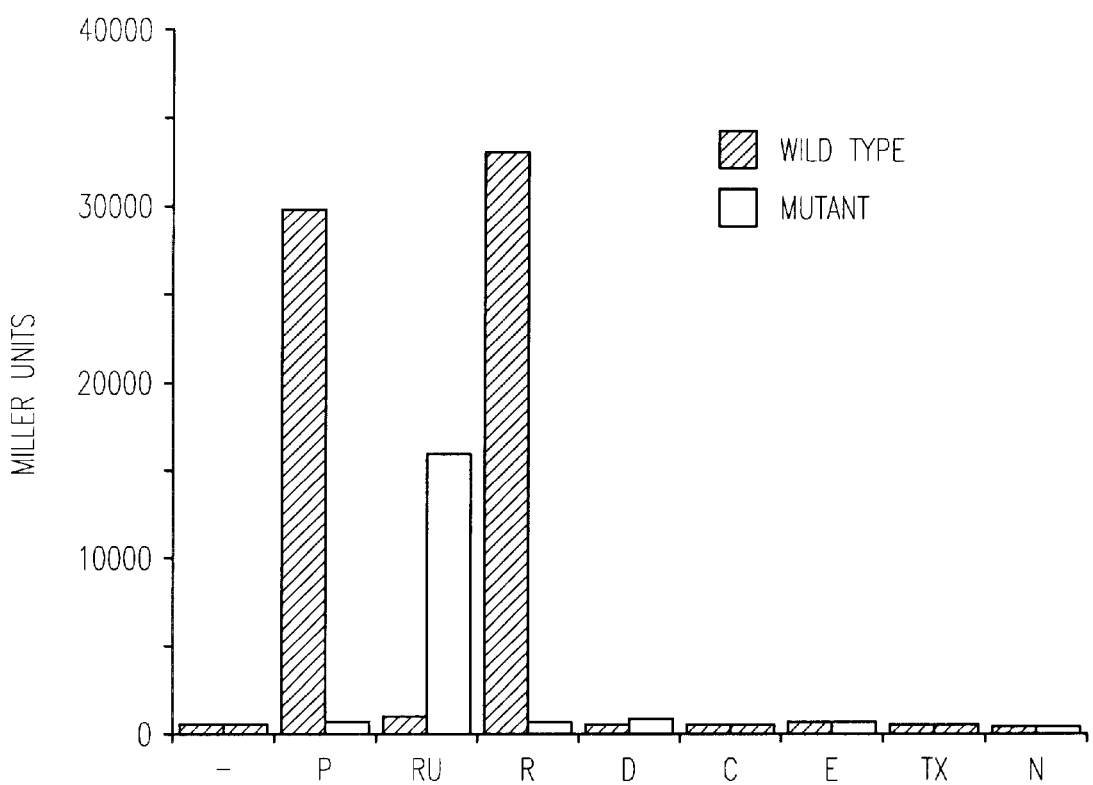

In panel (B), transcriptional activities of wild type and UP-1 mutant receptors were assayed in the presence of 1 μM progesterone (P), RU486 (RU), R5020 (R), dexamethasone (D), cortisol (C), estradiol (E), tamoxifen (TX) or nafoxidine (N) (see FIG. 5B). The synthetic agonist R5020 had no effect on the UP-1 mutant, suggesting that agonists, such as progesterone and R5020, require the C-terminus of the native receptor for binding and consequently fail to recognize the truncated UP-1 receptor. Other steroids known to enter yeast cells, such as estradiol, the antiestrogens tamoxifen and nafoxidine, dexamethasone and cortisol, might possibly activate the mutated receptor. All steroids tested were found to be inactive with either the wild type or mutant receptor. Thus, the activation of the mutant receptor is specific to antiprogestins.

Transcriptional Activity of Mutant Receptors in Mammalian Cells

FIG. 6 shows the transient transfection of mutant hPR into mammalian cells. In panel (A), HeLa cells were transiently transfected with phPR-B and pHPR-B891 receptors together with PRETKCAT receptor plasmid using the polybrene method of transfection as described (Tsai, et al. 1989). Cells were grown with or without 100 nM progesterone or RU486 for 48 hours prior to harvesting. CAT assays were performed as described above. In panel (B), CV-1 cells were transiently transfected as in (A).

With reference to FIG. 6, mutant receptor activity was assayed in both human endometrial HeLa cells and monkey kidney CV-1 fibroblasts. A mutant, phPR-891, was constructed by replacing the full-length PR insert of phPR-B vector with the truncated PR cDNA of YEphPR-B891. The resulting receptor mutant, phPR-B891, is a 42 amino acid truncation of hPR-B form. Mutant 891 and wild type receptors were transfected into HeLa cells together with the PRETKCAT reporter plasmid, which contains two copies of a GRE/PRE element.

Figure 6A:
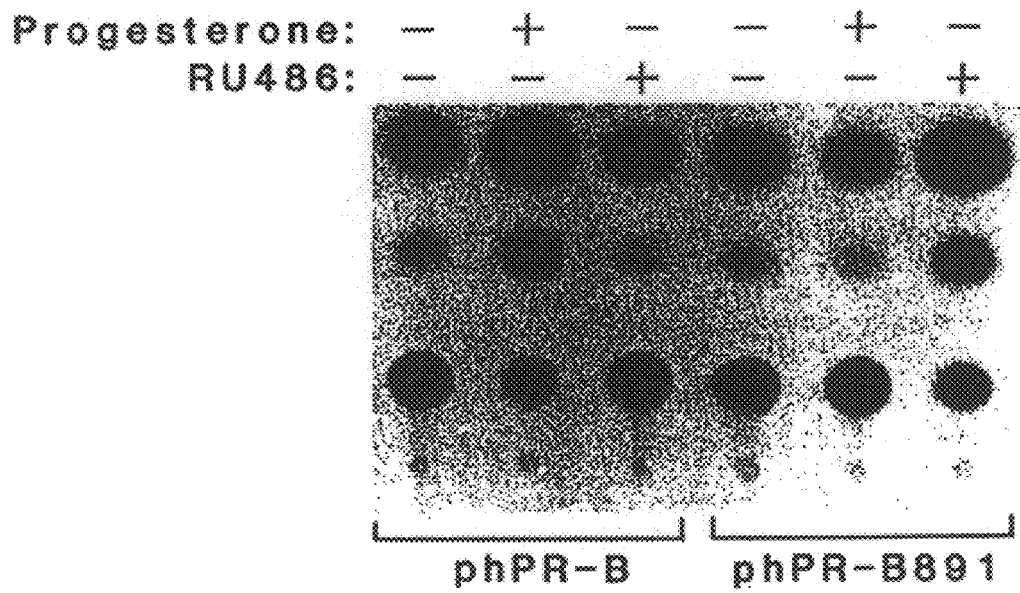
FIGS. 6A–B depicts the transient transfection of mutant human progesterone human receptor into mammalian cells.

As expected, wild type PR activated transcription of the CAT gene reporter in the presence of $10^{-7}$M progesterone (FIG. 6A). Although basal transcription level was high, a 3- to 4-fold induction of transcription was detected when progesterone was added to the media. In contrast, no induction occurred in the presence of RU486. The high basal level of transcription detected in these experiments may mask or alter an RU486 effect on wild type hPR.

On the other hand, an induction of CAT activity was observed when the 891 mutant was incubated in the presence of $10^{-7}$M RU486 (FIG. 6A). The same concentration of progesterone had no activity.

Figure 6B:
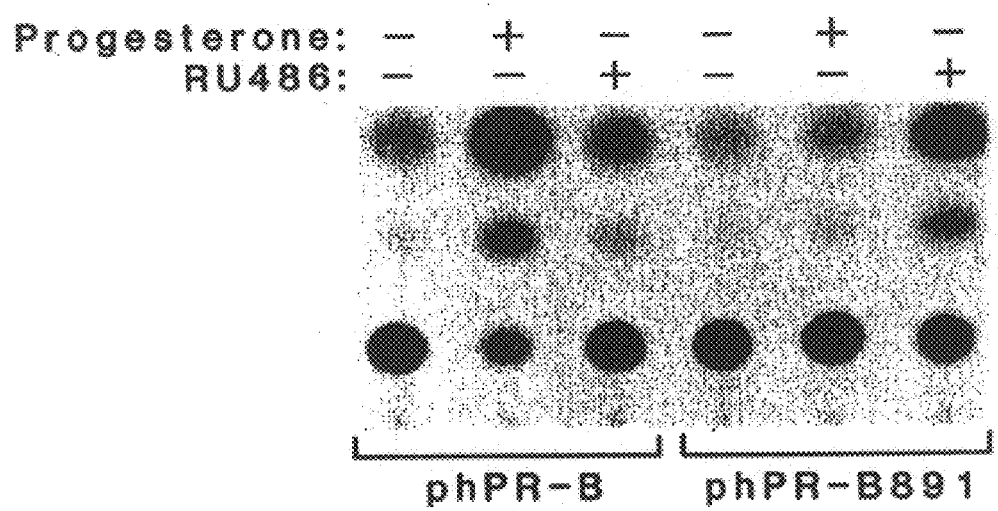

Cell-type specific factors can influence the activity of the transactivating domains of steroid receptors. In order to evaluate this possibility, wild type and mutant receptors were transfected into CV-1 cells. Similar results were obtained, i.e., progesterone activated the wild type receptor while RU486 activated 891 mutant receptor (FIG. 6B).

The protein synthesized from phPR-B891 plasmid was of the correct molecular weight in mammalian cells. The mutant receptor was transfected into COSMG cells. Western analysis on cell extracts showed that the 891 mutant was synthesized, as expected, as a protein of 109 kDa, which corresponds to a protein 42 amino acids shorter than the wild type hPR. Thus, RU486 acts as an agonist of the truncated B-receptor in a yeast reconstituted system and also in mammalian cells. The mechanism of transactivation does not require the C-terminal tail of the mutant receptor and is conserved between the three species tested.

Construction, Characterization and Analysis of Mutant Human GR-PR Fusion Protein Receptors
Plasmid Construction A mutated human Progesterone Receptor was constructed and characterized as discussed above. Mutagenesis of the ligand binding domain of the human PR was carried out under the same procedures outlined above. Characterization of the mutant progesterone receptor identified a single nucleotide deletion at base 2636. This mutation resulted in a shift of the reading frame which generates a stop codon 36 nucleotides downstream. As a result, the wild type receptor is truncated by 54 authentic amino acids and 12 novel amino acids are added at the c-terminus. The 42 amino acid truncation to the c-terminus was capable of binding RU486 and characterized as discussed above.

Plasmid DNA encoding the GR-PR fusion protein receptor and the wild type GR were constructed as follows. Each insertional mutant was digested with the restriction enzymes BamH1 and Xhol, which flanked the 3' side of the SV40 polyadenylation signal. The resulting fragments were isolated from an agarose gel. The large fragment of the insertional mutant containing the amino-terminal coding portion of the GR, i.e., the transregulatory and DNA binding region, and the bulk of the plasmid were ligated with the small fragment of another insertional mutant containing the carboxyl terminal coding sequence of the hPR deletion mutant prepared above. The resulting plasmids carrying the deletion in the hPR ligand binding domain were sequenced to ensure the integrity of the GR-PR mutant constructs.

In addition, plasmid DNA encoding a mutated rat or human GR and the wild type rat or human GR were also constructed. The plasmids for rat pGR0385 (or prCS1. C) and its wild type pGR0384 were constructed using the above methods. Details regarding construction, mutation and characterization of the above plasmid can be found in Lanz and Rusconi, *Endocrinology* 135:2183–2195 (1994), all of which is hereby incorporated by reference, including drawings. Characterization of the rat and human mutant GR identified a double point mutation in the ligand binding domain. In the rat construct, amino acids 770, 771, methonine and leucine, were substituted with alanine and alanine. Amino acids 780 and 781 were deleted. In the human constructs, amino acids 762 and 763 were deleted. Amino acids 752 and 753 were substituted with alanines. Both the substitution and deletion changes were at the carboxyl terminus portion of the rat or human GR ligand binding domain. The insertional mutant was digested with the restriction enzymes BamH1 and Xhol, which flank the 3' side of the SV40 polyadenylation signal and the resulting fragment was isolated from agarose gel. The large fragment of one insertional mutant containing the amino-terminal coding portion of the rat or human GR and the bulk of the plasmid were ligated with the small fragment of another insertional mutant containing the carboxy-terminal coding sequences of the mutated ligand binding domain. The resulting plasmids carrying the deletion in the ligand binding domain were sequenced to ensure the integrity of the rat or human GR mutants.

Figures 10, 11:
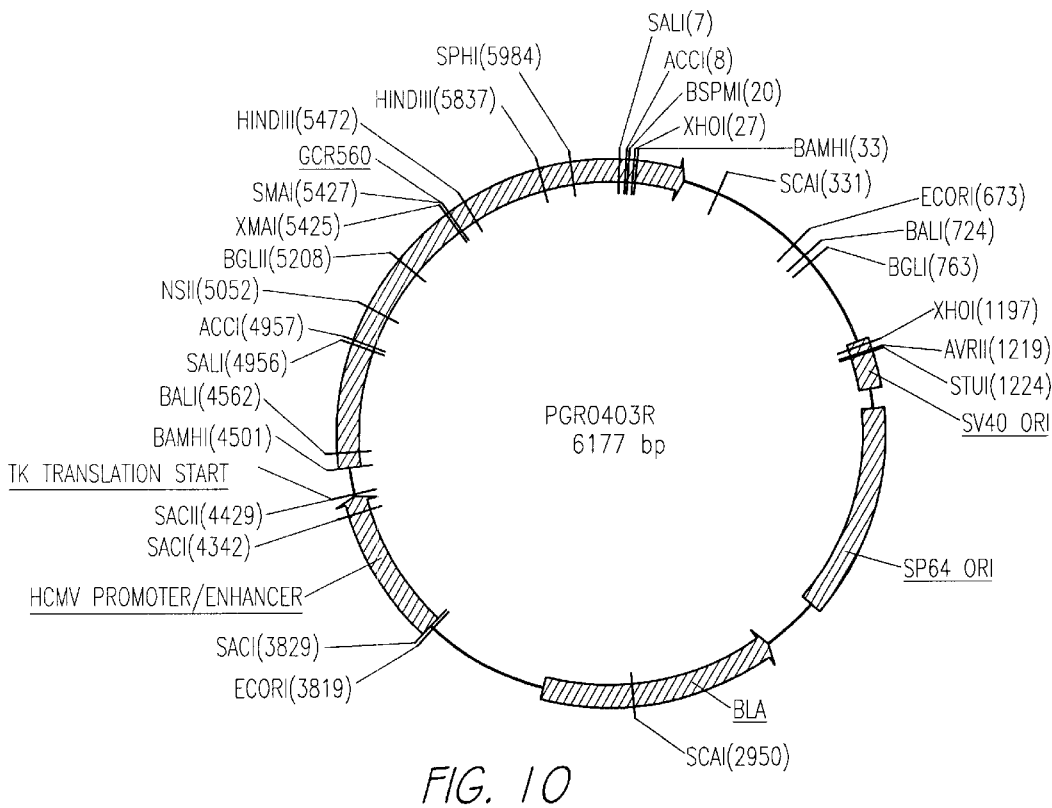
FIG. 10 depicts plasmid pGR0403R expressing a constitutively active mutant GR protein.
FIG. 11 illustrates the amount of CAT protein produced in response to ligand binding to mutant human and rat GR and the respective wild type receptors.
Figure 12:
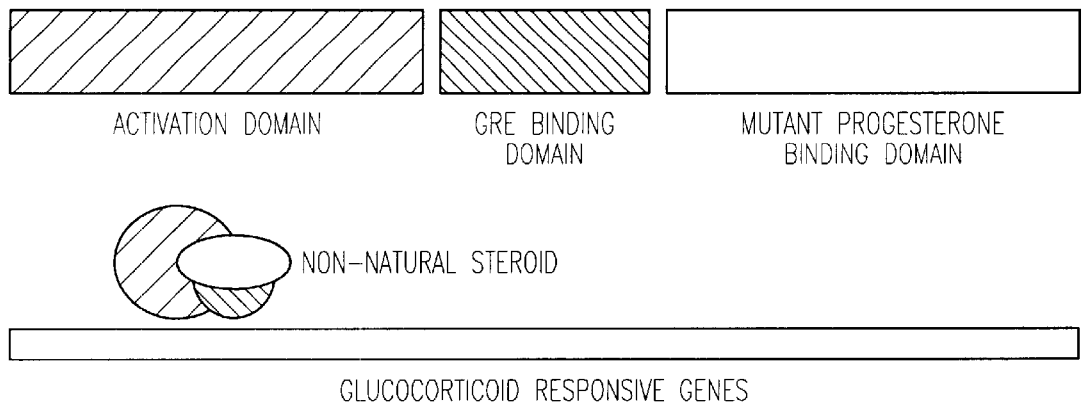
FIG. 12 is a schematic representation of the fusion protein with an activation transregulatory domain.
Figure 13:
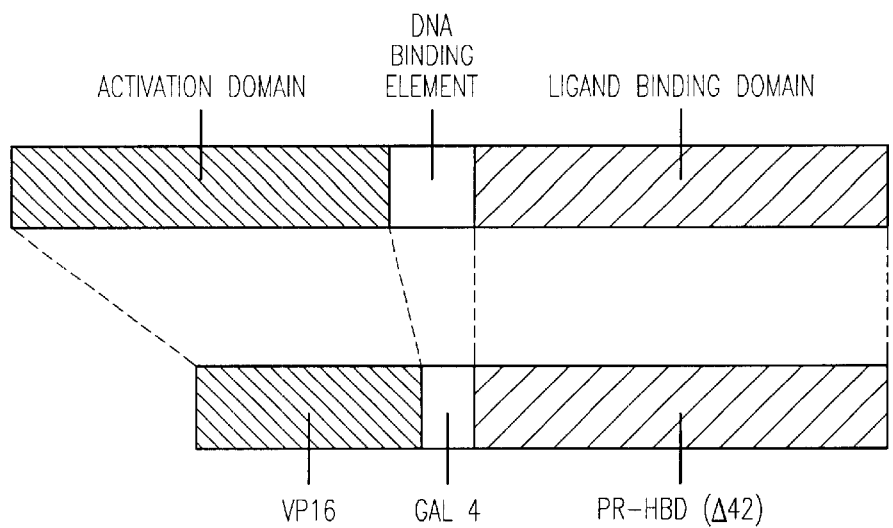
FIG. 13 is a schematic representation of the gene switch.

In addition, the above procedures were also used to construct plasmid DNA encoding a GR mutant with a constitutively active receptor, i.e., pGR0403R (FIGS. 9 and 10). The insertional mutant was digested with the appropriate restriction enzyme. The resulting fragments were isolated from agarose gel. The large fragment of the insertional mutant containing the amino-terminal coding portion of the GR, i.e., the transregulatory domains and DNA binding domains, and the bulk of the plasmid were ligated with the small fragment of another insertional mutant containing the mutated GR ligand binding domain. The resulting plasmid was sequenced (FIG. 9) to ensure integrity of the mutant construct.

Cell Culture, Transfection and Assay of CAT and Luciferase Activities

CV-1 cells were maintained at 37° C. in Dulbecco modified Eagle medium containing 10% fetal bovine serum ("FBS") in a humidified atmosphere containing 5% $CO_2$. Cells were transfected using the commercially available cationic agent lipofectamine. Briefly, DNA was mixed with the lipofectamine reagent and added to cells. After 5 hours, the DNA mix was removed and replaced with growth medium containing 10% FBS and cells were returned to an atmosphere containing 5% CO2. Eighteen hours later, cells were treated with steroids at various concentrations for approximately 24 hours, then harvested.

In this method, the CV1 cells are transformed with either the wild-type receptor or the mutant receptor and a glucocorticoid responsive reporter construct. To measure transcriptional activation, a CAT reporter containing two synthetic GRE's and a TATA box was used. To measure transcriptional repression, two constructs were used. The first contains two copies of the binding site for the inflammation-inducible transcription factor AP-1, following by the thymidine kinase (tk) promoter, linked to CAT. The second contains two copies of the binding site for the inflammation-inducible transcription factor $NF_K$-B, followed by a TATA box, linked to the luciferase gene. CAT expression was quantified using an ELISA assay following the manufacturer's recommended procedure. Luciferase activity was measured using a commercially-available luciferase assay following the manufacturer's recommended procedure.

In vitro Transfections Using CV1 Cells

The GR-PR fusion protein receptor and the mutant rat GR were tested for biological activity through in vitro transfection into CV1 cells. As controls vectors expressing the wild type human GR and the wild type rat GR were used. Results from these experiments demonstrate that the wild type human and wild type rat GR are transcriptionally activated in response to dexamethasone and minimally by RU486. In contrast, the mutant rat GR (CS1.CD) is transcriptionally activated by RU486 and not by dexamethasone. Similarly, the GR-PR fusion protein receptor is also activated by RU486 and not by dexamethasone. FIG. 11 illustrates the amount of CAT protein produced in response to the particular ligand.

In vitro Transcriptional Repression Studies

The transcriptional repression mediated by the mutant rat GR and human GR-PR construct were examined. The amount of CAT protein produced under the transcriptional control of synthetic activation elements was determined.

Specifically two reporter were examined TRE2tkCAT, which contains AP-1 fused to the thymidine kinase promoter linked to CAT. The second reporter used was $NF_K$-B-luc plasmid, which contains 2 $NF_K$-B binding sites fused to luciferase. These promoters contain inflammation-inducible promoters, and were used to evaluate the ability of the wild-type and mutant GR constructs to repress transcription.

Cells were transfected into CV1 cells along with either the wild type rat or human GR or the mutant rat (CS1.CD) or human GR. Cells pretreated with dex or RU486 to allow binding to the steroid receptor, were then stimulated with phorbol ester TPA to activate AP-1 and $NF_K$-B. Companion cells were not stimulated with TPA, and control cells also received neither dex nor RU486.

The results demonstrate that RU486 treatment resulted in a decrease in the level of CAT protein and luciferase activity in CSI.CD transfected cells. Dex treatment had no effect on CAT levels or luciferase. This was not expected results since dex does not bind to the ligand binding domain of the mutant rat GR CSI.CD or human GR. In cells transfected with the wild type GR both dex and RU486 caused a decrease in the level of CAT protein and luciferase activity. Such results are not unexpected because the wild type GR binds both dex and RU486.

RU486 acts through the mutated GR to repress transcription of AP1 driven genes. Since AP-1 and $NF_K$-B drive expression of pro-inflammatory genes, and RU486 acts through mutant or represses transcription of the AP-1 and $NF_K$-B driven genes, there was mediation of the anti-inflammation.

Mutant GR Expression and Detection

Three antibodies were obtaining and used to recognize recombinant partially purified GR in a Western blot analysis. Studies were performed to detect wild type GR and mutant GR protein from transfected cells or GR from rat synovial tissue using the above antibodies.

The antibodies also were able to detect human GR obtained from HeLa cell extracts. Significant levels of GR were detected with as low as 200 ug of whole cell extract. Immunoreactivity was also detected with synovial tissue, and antibodies are being prepared to distinguish between wild type and mutant GR proteins.

Transactivation and Transrepression Studies

In addition to the experiments above, the vector with $NF_K$-B binding sites fused to the luciferase gene, was injected into synovial joints in rats and treated with and without TNF-α. TNF-α is a cytokine which induces inflammation and promotes $NF_K$-B binding to its appropriate DNA sequences. With the DNA construct, TNF-α treatment results in an increase in transcription of TNF-α and exogenously-introduced luciferase gene. No luciferase activity in synovial tissue is detected without plasmid transfection. Also, there is no luciferase activity in synovial tissue injected with plasmid in the absence of TNF. A six-fold increase in the level of luciferase occurred when tissue was exposed to 0.1 or 1nM TNF. This serves as an easily detectable in vivo marker for wild-type or mutant GR function.

Construction, Characterization and Analysis of Double Point Mutations in the Ligand Binding Domain of GR Mutagenesis of the Ligand Binding Domain of Human GR A plasmid was constructed containing the human GR cDNA with amino acids 752 and 753 changed to alanines and amino acids 762 and 763 deleted. This plasmid, pSTC-hGRCS1/CD, was constructed as follows. The wild type glucocorticoid hormone receptor plasmid was digested with the restriction enzymes NsiI and XbaI, which flank the region to be mutated. The resulting fragments were isolated from agarose gel. The smaller fragment was digested with the restriction enzymes EcoRI and SspI, generating three fragments. The fragments were isolated from an agarose gel.

A synthetic fragment was synthesized: 5'-AAT TCC CCG AGG CGG CAG CTG AAA TCA TCA CCA ATC AGA TCT-3' (SEQ. ID. NO. 6) to replace the EcoRI-SspI fragment. The larger plasmid fragment, the NsiI-EcoRI fragment, the SspI-XbaI fragment and the synthetic EcoRI-SspI fragment were ligated together. The resulting plasmid carries the substitution and deletion as described above.

Characterization of GR Mutants in the Licand Binding Domain

To ensure the integrity of the mutation, the plasmid containing the mutant human GR was sequenced. Further experiments, as discussed above, were done to characterize the mutant human GR. Western analysis and hormone binding as discussed above were performed to ensure character of the constructs, e.g., cell expression of the protein and steroid specificity for activation or repression of transcription.

Transcriptional Activity of the Mutant Receptors in Mammalian Cells

LMTK⁻cells were maintained at 370° C. in Bulbecco's modified Eagle's medium containing 10% fetal Bovine serum ("FBS") in a humidified atmosphere containing 5% CO2. Cells were transfected with the polybrene method described in Kawai et al., *Mol. Cell. Bio.* 4:91–1172 (1984), hereby incorporated by reference, including drawings. After a 25% glycerol shock in Hank's buffered saline solution ("HBSS"), the cells were washed twice with HBSS and medium was added containing hormones or solvent. The cells were cultured for 48 hours. Extracts were made by freeze-thawing. CAT activity was assayed with 25 μg protein and an incubation time of 16 hours. CAT activity assayed as described by Seed et al., *Gene* 67:271 (1988), hereby incorporated by reference, including drawings.

Construction, Characterization and Analysis of Constitutively Active Mutant GR

Mutagenesis of the Ligand Binding Domain of Human GR

Deletion of the steroid ligand binding domain was prepared as follows. This deletion removed a large portion of the of the carboxyl-terminal portion of the protein eliminating all steroid binding properties. Using the procedures discussed above, the pGR0403R plasmid (FIGS. 9 and 10) was constructed. This mutation gave rise to a constitutively active receptor. This mutant was able to activate transcription of the CAT reporter gene in the presence or absence of glucocorticoid hormone. In addition, this mutant is also able to repress transcription of the $NF_K$-B-luciferase construct.

Characterization of GR Mutants in the Ligand Binding Domain

To ensure the integrity of the mutation, the plasmid containing the mutant human GR, pGR0403R (FIG. 10) was sequenced (FIG. 9). Further experiments, as discussed above, were done to characterize the mutant human GR. Western analysis and hormone binding as discussed above were performed to ensure character of the constructs, e.g., cell expression of the protein, lack of steroid specificity for activation or repression of transcription and base level of gene expression as compared to constitutive expression.

Transcriptional Activity of the Mutant Receptors in Mammalian Cells

The constitutively active mutant GR construct was prepared as discussed above. The receptor has no ligand binding domain and, when expressed in cells, represses transcription of AP-1 driven genes in the absence of dex or RU486. In vitro testing shows that the constitutively active GR mutant when transfected constitutively activates promoters with glucocorticoid responsive elements and represses AP-1 containing promoters.

Construction, Characterization and Analysis of Mutations in the DNA Binding or Transreculatory Domains of GR Mutagenesis of the DNA Binding or Transregulatory Domains of GR For obtaining transactivation activity without transrepression activity the following construct was made. The mutated ligand binding domain is mutated as described above. Procedure details from Lanz, et al., *Endocrinology* 135:2183–2195 (1994) are hereby incorporated by reference, including drawings. The mutated DNA binding domain is mutated by changing the serine at position 425 to glycine, the leucine at position 436 to valine and the tyrosine and asparagine at positions 478 and 479 to leucine and glycine.

For obtaining transrepression activity without transactivation, the following construct was made. The mutated ligand binding domain is mutated as described above. The mutated transregulatory domain is mutated by changing the alanine at position 458 to threonine, the asparagine and alanine at positions 454 and 458 to aspartic acid and threonine, respectively, and the arginine and aspartic acid at positions 460 and 562 to aspartic and cysteine, respectively.

Characterization of GR Mutants in the DNA Binding or Transregulatory Domains

To ensure the integrity of the mutation, the plasmids containing the mutant GR were sequenced. Further experiments, as discussed above, were done to characterize the mutant GR constructs. Western analysis and hormone binding as discussed above were performed to ensure character of the constructs, e.g., protein expression in cells and steroid specificity for activation or repression of transcription.

Transcriptional Activity of the Mutant Receptors in Mammalian Cells

The above mutant GR constructs were prepared. The two different receptor constructs have either a mutated DNA binding domain or a mutated transregulatory domain. When expressed in cells, the transrepression only construct with a DNA binding domain mutation represses transcription of AP-1 and $NF_K$-B driven genes in the presence of dex or RU486. No activation of transcription was observed. In vitro testing shows that the GR mutant when transfected represses AP-1 and $NF_K$-B containing promoters and does not activate the glucocorticoid responsive genes.

As for the transactivation only construct with a mutated transregulatory domain, activation of transcription was observed in the presence of various steroids. In the presence of dex or RU486 no transrepression of AP-1 or $NF_K$-B driven genes was detected. In vitro testing shows that the GR mutant when transfected activates glucocorticoid responsive genes in response to ligand stimulation but no repression of AP-1 or $NF_K$-B genes was observed.

Chicken, Rat and Mammalian Progesterone Receptors

Chicken, rat and mammalian progesterone receptors are readily available and function by binding to the same DNA regulatory sequence. Chicken and rat progesterone receptors, however, binds a different spectrum of ligands, possessing affinities different from those interacting with human progesterone receptor. Thus, the chicken and rat progesterone receptor can be used as a transgene regulator in humans. Further, it can be used to screen for specific ligands which activate chicken or rat progesterone receptor but not endogenous human progesterone receptor. An example of a ligand is 5α-pregnane-3,20-dione (dihydroprogesterone) which binds extremely well to chicken and rat progesterone receptor but does not bind or binds very poorly to human progesterone receptor.

Although the unmodified chicken or rat progesterone receptors are already endowed with a different spectrum of ligand binding affinities from the human or other mammals and can be used in its native form, it is important to try to select additional mutated progesterone receptor to create a more efficacious receptor. The differences in chicken, rat and human progesterone receptors are due to a few amino acid differences. Thus, other mutations could be artificially introduced. These mutations would enhance the receptor differences. Screening receptor mutations for ligand efficacy produces a variety of receptors in which alterations of affinity occur. The initial screening of progesterone mutants was carried out using intermediate levels of ligands. One mutant had lost progesterone affinity entirely, but bound a synthetic ligand RU486 with nearly wild-type efficiency. RU486 is normally considered an antagonist of progesterone function, but had become an agonist when tested using this specific mutant. Because the ligand is synthetic, it does not represent a compound likely to be found in humans or animals to be treated with gene therapy. Although RU486 works as an agonist in this case, it is not ideal because of its potential side effects as an anti-glucocorticoid. Further, it also binds to the wild-type human progesterone. Thus, it has the undesirable side effect of reproductive and endocrine disfunction.

This approach is not limited to the progesterone receptor, since it is believed that all ligand activated transcription factors act through similar mechanisms. One skilled in the art recognizes that similar screening of other members of the steroid superfamily will provide a variety of molecular switches. For example, the compound 1,25-dihydroxy-Vitamin $D_3$ activates the Vitamin D receptor but the compound 24,25-dihydroxy-Vitamin D does not. Mutants of the Vitamin D receptor can be produced which are transcriptionally activated when bound to 24,25-dihydroxy-Vitamin D, but not by 1,25-Vitamin $D_3$.

One skilled in the art recognizes that the ligands are designed to be physiologically tolerated, easily cleared, non-toxic and have specific effects upon the transgene system rather than the entire organism.

Transgenic Animals

A modified glucocorticoid receptor can be used in the production of transgenic animals. A variety of procedures are known for making transgenic animals, including that described in Leder and Stewart, U.S. Pat. No. 4,736,866 issued Apr. 12, 1988, and Palmiter and Bannister, *Annual Review of Genetics*, 20:465–499. For example, the mutated glucocorticoid receptors described above can be combined with the nucleic acid cassette containing the recombinant gene to be expressed. For example, lactoferrin can be placed under the control of a basal promoter, such as thymidine kinase promoter with adjacent glucocorticoid responsive elements. This vector is introduced into the animal germ lines, along with the vector constitutively expressing the mutant glucocorticoid receptor. The two vectors can also be combined into one vector. The expression of the recombinant gene in the transgenic animal is turned on or off by administering a pharmacological dose of RU 38486 to the transgenic animal. This hormone serves to specifically activate transcription of the transgene. The dose can be adjusted to regulate the level of expression. One skilled in the art will readily recognize that this protocol can be used for a variety of genes and, thus, it is useful in the regulation of temporal expression of any given gene product in transgenic animals.

Methods of Use
Cell Transformation

One embodiment of the present invention includes cells transformed with nucleic acid encoding for the mutated receptor. Once the cells are transformed, the cells will express the protein, polypeptide, or RNA encoded for by the nucleic acid. Cells include but are not limited to joints, lungs, muscle and skin. This is not intended to be limiting in any manner.

The nucleic acid which contains the genetic material of interest is positionally and sequentially oriented within the host or vectors such that the nucleic acid can be transcribed into RNA and, when necessary, be translated into proteins or polypeptides in the transformed cells. A variety of mutated glucocorticoid proteins and polypeptides can be expressed by the sequence in the nucleic acid cassette in the transformed cells.

Transformation can be done either by in vivo or ex vivo techniques. One skilled in the art will be familiar with such techniques for transformation. Transformation by ex vivo techniques includes co-transfecting the cells with DNA containing a selectable marker. This selectable marker is used to select those cells which have become transformed. Selectable markers are well known to those who are skilled in the art.

For example, one approach to gene therapy for muscle diseases is to remove myoblasts from an affected individual, genetically alter them in vitro, and reimplant them into a receptive locus. The ex vivo approach includes the steps of harvesting myoblasts cultivating the myoblasts, transducing or transfecting the myoblasts, and introducing the transfected myoblasts into the affected individual.

The myoblasts may be obtained in a variety of ways. They may be taken from the individual who is to be later injected with the myoblasts that have been transformed or they can be collected from other sources, transformed and then injected into the individual of interest.

Once the ex vivo myoblasts are collected, they may be transformed by contacting the myoblasts with media containing the nucleic acid transporter and maintaining the cultured myoblasts in the media for sufficient time and under conditions appropriate for uptake and transformation of the myoblasts. The myoblasts may then be introduced into an appropriate location by injection of cell suspensions into tissues. One skilled in the art will recognize that the cell suspension may contain: salts, buffers or nutrients to maintain viability of the cells; proteins to ensure cell stability; and factors to promote angiogenesis and growth of the implanted cells.

In an alternative method, harvested myoblasts may be grown ex vivo on a matrix consisting of plastics, fibers or gelatinous materials which may be surgically implanted in an appropriate location after transduction. This matrix may be impregnated with factors to promote angiogenesis and growth of the implanted cells. Cells can then be reimplanted.

Administration

Administration as used herein refers to the route of introduction of a vector or carrier of DNA into the body. Administration may include intravenous, intramuscular, topical, or oral methods of delivery. Administration can be directly to a target tissue or through systemic delivery.

In particular, the present invention can be used for treating disease or for administering the formulated DNA expression vectors capable of expressing any specific nucleic acid sequence. Administration can also include administering a regulatable vector discussed above. Such administration of a vector can be used to treat disease. The preferred embodiment is by direct injection to the target tissue or systemic administration.

A second critical step is the delivery of the DNA vector to the nucleus of the target cell where it can express a gene product. In the present invention this is accomplished by formulation. The formulation can consist of purified DNA vectors or DNA vectors associated with other formulation elements such as lipids, proteins, carbohydrates, synthetic organic or inorganic compounds. Examples of such formulation elements include, but are not limited to, lipids capable of forming liposomes, cationic lipids, hydrophilic polymers, polycations (e.g., protamine, polybrene, spermidine, polylysine), peptide or synthetic ligands recognizing receptors on the surface of the target cells, peptide or synthetic ligands capable of inducing endosomal lysis, peptide or synthetic ligands capable of targeting materials to the nucleus, gels, slow release matrices, soluble or insoluble particles, as well as other formulation elements not listed. This includes formulation elements for enhancing the delivery, uptake, stability, and/or expression of genetic material into cells.

The delivery and formulation of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

DNA uptake by cells associated with fluid spaces have the unique ability to take up DNA from the extracellular space after simple injection of purified DNA preparations into the fluid spaces. Expression of DNA by this method can be sustained for several months.

Incorporating DNA by formulation into particulate complexes of nanometer size that undergo endocytosis increases the range of cell types that will take up foreign genes from the extracellular space.

Formulation can also involve DNA transporters which are capable of forming a non-covalent complex with DNA and directing the transport of the DNA through the cell membrane. This may involve the sequence of steps including endocytosis and enhanced endosomal release. It is preferable that the transporter also transport the DNA through the nuclear membrane. See, e.g., the following applications all of which (including drawings) are hereby incorporated by reference herein: (1) Woo et al., U.S. Ser. No. 07/855,389, now abandoned, entitled "A DNA Transporter System and Method of Use" filed Mar. 20, 1992; (2) Woo et al., PCT/US93/02725, entitled "A DNA Transporter System and method of Use", (designating the U.S. and other countries) filed Mar. 19, 1993; and (3) continuation-in-part application by Woo et al., entitled "Nucleic Acid Transporter Systems and Methods of Use", filed Dec. 14, 1993, now U.S. Pat. No. 6033884.

In addition, delivery can be cell specific or tissue specific by including cell or tissue specific promoters. Furthermore, mRNA stabilizing sequences (3' UTR's) can be used to provide stabilized modified receptor molecules. Such stabilizing sequences increase the half-life of mRNAs and can be cell or tissue specific. The above is discussed in more detail in U.S. Pat. No. 5,298,422 (Schwartz et al.) and U.S.

application Ser. No. 08/209,846 (Schwartz et al.), filed Mar. 9, 1994, entitled "Expression Vector Systems and Method of Use, now U.S. Pat. No. 5756264." Both of these, the whole of which, are incorporated by reference herein, including drawings.

In a preferred method of administration involving a DNA transporter system, the DNA transporter system has a DNA binding complex with a binding molecule capable of non-covalently binding to DNA which is covalently linked to a surface ligand. The surface ligand is capable of binding to a cell surface receptor and stimulating entry into the cell by endocytosis, pinocytosis, or potocytosis. In addition, a second DNA binding complex is capable of non-covalently binding to DNA and is covalently linked to a nuclear ligand. The nuclear ligand is capable of recognizing and transporting a transporter system through a nuclear membrane. Additionally, a third DNA binding complex may be used which is also capable of non-covalently binding to DNA. The third binding molecule is covalently linked to an element that induces endosomal lysis or enhanced release of the complex from the endosome after endocytosis. The binding molecules can be spermine, spermine derivatives, histones, cationic peptides and/or polylysine. See also Szoka, C. F., Jr. et al., Bioconjug. Chem. 4:85–93 (1993); Szoka, F. C., Jr. et al., P.N.A.S., 90:893–897 (1993).

Transfer of genes directly has been very effective. Experiments show that administration by direct injection of DNA into joint tissue results in expression of the gene in the area of injection. Injection of plasmids containing the mutated receptors into the spaces of the joints results in expression of the gene for prolonged periods of time. The injected DNA appears to persist in an unintegrated extrachromosomal state. This means of transfer is the preferred embodiment.

The formulation used for delivery may also be by liposomes or cationic lipids. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active. Cationic lipid formulations such as formulations incorporating DOTMA has been shown to deliver DNA expression vectors to cells yielding production of the corresponding protein. Lipid formulations may be non-toxic and biodegradable in composition. They display long circulation half-lives and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system. See Szoka, F. C., Jr. et al., Pharm. Res., 7:824–834 (1990); Szoka, F. C., Jr. et al., Pharm. Res., 9:1235–1242 (1992).

The chosen method of delivery should result in nuclear or cytoplasmic accumulation and optimal dosing. The dosage will depend upon the disease and the route of administration but should be between 1–1000 µg/kg of body weight. This level is readily determinable by standard methods. It could be more or less depending on the optimal dosing. The duration of treatment will extend through the course of the disease symptoms, possibly continuously. The number of doses will depend upon disease, the formulation and efficacy data from clinical trials.

With respect to vectors, the pharmacological dose of a vector and the level of gene expression in the appropriate cell type includes but is not limited to sufficient protein or RNA to either: (1) increase the level of protein production; (2) decrease or stop the production of a protein; (3) inhibit the action of a protein; (4) inhibit proliferation or accumulation of specific cell types; and (5) induce proliferation or accumulation of specific cell types. As an example, if a protein is being produced which causes the accumulation of inflammatory cells within the joint, the expression of this protein can be inhibited, or the action of this protein can be interfered with, altered, or changed.

Persistent ExPression Usincr Episomal Vectors

In each of the foregoing examples, transient expression of recombinant genes induces the desired biological response. In some diseases more persistent expression of recombinant genes is desirable. This is achieved by adding elements which enable extrachromosomal (episomal) replication of DNA to the structure of the vector. Vectors capable of episomal replication are maintained as extrachromosomal molecules and can replicate. These sequences will not be eliminated by simple degradation but will continue to be copied. Episomal vectors provide prolonged or persistent expression, though not necessarily stable or permanent, expression of recombinant genes in the joint. Persistent as opposed to stable expression is desirable to enable adjustments in the pharmacological dose of the recombinant gene product as the disease evolves over time.

Formulations for Gene Delivery into Cells of the Joint

Initial experiments used DNA in formulations for gene transfer into cells of the joint. This DNA is taken up by synovial cells during the process of these cells continually resorbing and remodeling the synovial fluid by secretion and pinocytosis. Gene delivery is enhanced by packaging DNA into particles using cationic lipids, hydrophilic (cationic) polymers, or DNA vectors condensed with polycations which enhance the entry of DNA vectors into contacted cells. Formulations may further enhance entry of DNA vectors into the body of the cell by incorporating elements capable of enhancing endosomal release such as certain surface proteins from adenovirus, influenza virus hemagglutinin, synthetic GALA peptide, or bacterial toxins. Formulations may further enhance entry of DNA vectors into the cell by incorporating elements capable of binding to receptors on the surface of cells in the joint and enhancing uptake and expression. Alternatively, particulate DNA complexed with polycations can be efficient substrates for phagocytosis by monocytes or other inflammatory cells. Furthermore, particles containing DNA vectors which are capable of extravasating into the inflamed joint can be used for gene transfer into the cells of the joint. One skilled in the art will recognize that the above formulations can also be used with other tissues as well.

Induction of "Steroid Response" by Gene Transfer of Steroid Receptors into Cells of the Joint Current therapy for severe arthritis involves the administration of pharmacological agents including steroids to depress the inflammatory response. Steroids can be administered systemically or locally by direct injection into the joint space.

Steroids normally function by binding to receptors within the cytoplasm of cells. Formation of the steroidreceptor complex changes the structure of the receptor so that it becomes capable of translocating to the nucleus and binding to specific sequences within the genome of the cell and altering the expression of specific genes. Genetic modifications of the steroid receptor can be made which enable this receptor to bind non-natural steroids. Other modifications can be made to create a mutated steroid receptor which is "constitutively active" meaning that it is capable of binding to DNA and regulating gene expression in the absence of steroid in the same way that the natural steroid receptor regulates gene expression after treatment with natural or synthetic steroids.

Of particular importance is the effect of glucocorticoid steroids such as cortisone, hydrocortisone, prednisone, or dexamethasone which are effective drugs available for the treatment of arthritis. One approach to treating arthritis is to introduce a vector in which the nucleic acid cassette expresses a genetically modified steroid receptor into cells of the joint, e.g., a genetically modified steroid receptor which mimics the effect of glucocorticoid but does not require the presence of glucocorticoid for effect. This is achieved by expression of a fusion receptor protein discussed above or other mutated glucocorticoid receptors such as ones which are constitutively active within cells of the joint. This induces the therapeutic effects of steroids without the systemic toxicity of these drugs.

Alternatively, construction of a steroid receptor which is activated by a novel, normally-inert steroid enables the use of drugs which would affect only cells taking up this receptor. These strategies obtain a therapeutic effect from steroids on arthritis without the profound systemic complications associated with these drugs. Of particular importance is the ability to target these genes differentially to specific cell types (for example synovial cells versus lymphocytes) to affect the activity of these cells.

The steroid receptor family of gene regulatory proteins is an ideal set of such molecules. These proteins are ligand activated transcription factors whose ligands can range from steroids to retinoic acid, fatty acids, vitamins, thyroid hormones and other presently unidentified small molecules. These compounds bind to receptors and either activate or repress transcription.

The preferred receptor of the present invention is modification of the glucocorticoid receptor, i.e., the fusion protein receptor. These receptors can be modified to allow them to bind various ligands whose structure differs from naturally occurring ligands. For example, small C-terminal alterations in amino acid sequence, including truncation, result in altered affinity of ligand binding to the progesterone receptor. By screening receptor mutants, receptors can be customized to respond to ligands which do not activate the host cell endogenous receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor superfamily, such as receptors including the estrogen, progesterone, glucocorticoid-α, glucocorticoid-β, mineral corticoid, androgen, thyroid hormone, retinoic acid, and Vitamin D3 receptors.

Direct DNA Delivery to Muscle

Diseases that result in abnormal muscle development, due to many different reasons can be treated using the above modified glucocorticoid receptors. These diseases can be treated by using the direct delivery of genes encoding for the mutated glucocorticoid receptor of the present invention resulting in the production of mutated receptor gene product. Genes which can be repressed or activated have been outlined in detail above.

Direct DNA Delivery to the Lungs

Current therapy for severe asthma involves the administration of pharmacological agents including steroids to inhibit the asthma response. Steroids can be administered systemically or locally by direct instillation or delivery into the lungs.

Of particular importance is the effect of glucocorticoid steroids such as cortisone, hydrocortisone, prednisone, or dexamethasone which are the most important effective drugs available for the treatment of asthma. One approach to treating asthma is to introduce a vector in which the nucleic acid cassette expresses a genetically modified steroid receptor into cells of the lungs, e.g., a genetically modified steroid receptor which mimics the effect of glucocorticoid but does not require the presence of glucocorticoid for effect. This is achieved by expression of the fusion proteins discussed above or other mutated glucocorticoid receptors such as ones which are constitutively active within cells of the lungs. This induces the therapeutic effects of steroids without the systemic toxicity of these drugs.

Alternatively, construction of a steroid receptor which is activated by a novel, normally-inert steroid enables the use of drugs which would affect only cells taking up this receptor. These strategies obtain a therapeutic effect from steroids on asthma without the profound systemic complications associated with these drugs. Of particular importance is the ability to target these genes differentially to specific cell types (for example alveoli of the lungs) to affect the activity of these cells.

The steroid receptor family of gene regulatory proteins is an ideal set of such molecules. These proteins are ligand-activated transcription factors whose ligands can range from steroids to retinoids, fatty acids, vitamins, thyroid hormones, and other presently unidentified small molecules. These compounds bind to receptors and either up-regulate or down-regulate transcription.

The preferred receptor of the present invention is the modified glucocorticoid receptor. These receptors can be modified to allow them to bind various ligands whose structure differs from naturally occurring ligands. For example, small C-terminal alterations in amino acid sequence, including truncation, result in altered affinity of the ligand and altered function. By screening receptor mutants, receptors can be customized to respond to ligands which do not activate the host cells own receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor superfamily, such as receptors including the estrogen, progesterone, glucocorticoid-α, glucocorticoid-β, mineral corticoid, androgen, thyroid hormone, retinoic acid, and Vitamin D3 receptors.

Mutated Glucocorticoid Receptors as Gene Switch

In addition to the above methods, the mutated glucocorticoid receptors can be used as gene switches as described in U.S. Ser. No. 07/939,246, by Vegeto et al., filed Sep. 2, 1992, entitled "Mutated Steroid Hormone Receptors, Methods for Their Use and Molecular Switch for Gene Therapy," the whole of which (including drawings) is hereby incorporated by reference. The above constructs of the present invention can be used to express a co-transfected target therapeutic gene using a glucocorticoid response element ("GRE") containing promoter. The GRE promoter will drive, activate or transactivate expression of the therapeutic gene upon activation of the ligand binding domain of the constructs of the present invention. The therapeutic protein can be a secreted protein, e.g., an anti-inflammatory cytokine. Such methods allow more global effect on the transfected tissue.

One skilled in the art would readily appreciate that the present invention is well adapted to carry out the objects and obtain the ends and advantages mentioned, as well as those inherent therein. The mutated steroid receptors along with the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A plasmid designated as pGR0403R as depicted in SEQ ID NO:1.

2. An isolated host cell transformed with a plasmid of claim 1.

* * * * *

SEQUENCE LISTING

<160> NUMBER OF SEQ ID NOS: 6

<210> SEQ ID NO 1
<211> LENGTH: 6177
<212> TYPE: DNA
<213> ORGANISM: Artificial sequence
<220> FEATURE:
<221> NAME/KEY: misc_feature
<223> OTHER INFORMATION: Plasmid pGRO403R

<400> SEQUENCE: 1

```
ctagagtcga cctgcagccc aagctctcga gggatcctga gaacttcagg gtgagtttgg      60
ggacccttga ttgttctttc tttttcgcta ttgtaaaatt catgttatat ggaggggca      120 aagttttcag ggtgttgttt agaatgggaa gatgtccctt gtatcaccat ggaccctcat      180
gataattttg tttctttcac tttctactct gttgacaacc attgtctcct cttattttct      240
tttcattttc tgtaactttt tcgttaaact ttagcttgca tttgtaacga attttaaat      300 tcacttttgt ttatttgtca gattgtaagt actttctcta atcacttttt tttcaaggca      360
atcagggtat attatattgt acttcagcac agttttagag aacaattgtt ataattaaat      420
gataaggtag aatatttctg catataaatt ctggctggcg tggaaatatt cttattggta      480
gaaacaacta catcctggtc atcatcctgc ctttctcttt atggttacaa tgatatacac      540
tgtttgagat gaggataaaa tactctgagt ccaaaccggg cccctctgct aaccatgttc      600
atgccttctt cttttcccta cagctcctgg gcaacgtgct ggttgttgtg ctgtctcatc      660
attttggcaa agaattcact cctcaggtgc aggctgccta tcagaaggtg gtggctggtg      720
tggccaatgc cctggctcac aaataccact gagatctttt tccctctgcc aaaaattatg      780
gggacatcat gaagcccctt gagcatctga cttctggcta ataaggaaa tttatttttca      840 ttgcaatagt gtgttggaat tttttgtgtc tctcactcgg aaggacatat gggagggcaa      900
atcatttaaa acatcagaat gagtatttgg tttagagttt ggcaacatat gccatatgct      960
ggctgccatg aacaaaggtg gctataaaga ggtcatcagt atatgaaaca gccccctgct     1020
gtccattcct tattccatag aaaagccttg acttgaggtt agattttttt tatattttgt     1080
tttgtgttat ttttttcttt aacatcccta aaattttcct tacatgtttt actagccaga     1140
tttttcctcc tctcctgact actcccagtc atagctgtcc ctcttctctt atgaactcga     1200
ggagcttttt gcaaaagcct aggcctccaa aaaagcctcc tcactacttc tggaatagct     1260
cagaggccga ggcggcctcg gcctctgcat aaataaaaaa aattagtcag ccatgggcg      1320 gagaatgggc ggaactgggc ggagttaggg gcgggatggg cggagttagg ggcgggacta     1380
tggttgctga ctaattgaga ctgcattaat gaatcggcca acgcgcgggg agaggcggtt     1440
tgcgtattgg gcgctcttcc gcttcctcgc tcactgactc gctgcgctcg gtcgttcggc     1500
```

-continued

```
tgcggcgagc ggtatcagct cactcaaagg cggtaatacg gttatccaca gaatcagggg      1560
ataacgcagg aaagaacatg tgagcaaaag gccagcaaaa ggccaggaac cgtaaaaagg      1620
ccgcgttgct ggcgtttttc cataggctcc gcccccctga cgagcatcac aaaaatcgac      1680
gctcaagtca gaggtggcga acccgacag gactataaag ataccaggcg tttccccctg       1740
gaagctccct cgtgcgctct cctgttccga ccctgccgct taccggatac ctgtccgcct      1800
ttctcccttc gggaagcgtg gcgctttctc aatgctcacg ctgtaggtat ctcagttcgg      1860
tgtaggtcgt tcgctccaag ctgggctgtg tgcacgaacc ccccgttcag cccgaccgct      1920
gcgccttatc cggtaactat cgtcttgagt ccaacccggt aagacacgac ttatcgccac      1980
tggcagcagc cactggtaac aggattagca gagcgaggta tgtaggcggt gctacagagt      2040
tcttgaagtg gtggcctaac tacggctaca ctagaaggac agtatttggt atctgcgctc      2100
tgctgaagcc agttaccttc ggaaaaagag ttggtagctc ttgatccggc aaacaaacca      2160
ccgctggtag cggtggtttt tttgtttgca agcagcagat tacgcgcaga aaaaaggat       2220 ctcaagaaga tcctttgatc ttttctacgg ggtctgacgc tcagtggaac gaaaactcac      2280
gttaagggat tttggtcatg agattatcaa aaaggatctt cacctagatc cttttaaatt      2340
aaaaatgaag ttttaaatca atctaaagta tatatgagta aacttggtct gacagttacc      2400
aatgcttaat cagtgaggca cctatctcag cgatctgtct atttcgttca tccatagttg      2460
cctgactccc cgtcgtgtag ataactacga tacgggaggg cttaccatct ggccccagtg      2520
ctgcaatgat accgcgagac ccacgctcac cggctccaga tttatcagca ataaaccagc      2580
cagccggaag ggccgagcgc agaagtggtc ctgcaacttt atccgcctcc atccagtcta      2640
ttaattgttg ccgggaagct agagtaagta gttcgccagt taatagtttg cgcaacgttg      2700
ttgccattgc tacaggcatc gtggtgtcac gctcgtcgtt tggtatggct tcattcagct      2760
ccggttccca acgatcaagg cgagttacat gatccccat gttgtgcaaa aaagcggtta      2820
gctccttcgg tcctccgatc gttgtcagaa gtaagttggc cgcagtgtta tcactcatgg      2880
ttatggcagc actgcataat tctcttactg tcatgccatc cgtaagatgc ttttctgtga      2940
ctggtgagta ctcaaccaag tcattctgag aatagtgtat gcggcgaccg agttgctctt      3000
gcccggcgtc aatacgggat aataccgcgc cacatagcag aactttaaaa gtgctcatca      3060
ttggaaaacg ttcttcgggg cgaaaactct caaggatctt accgctgttg agatccagtt      3120
cgatgtaacc cactcgtgca cccaactgat cttcagcatc ttttactttc accagcgttt      3180
ctgggtgagc aaaaacagga aggcaaaatg ccgcaaaaaa gggaataagg gcgacacgga      3240
aatgttgaat actcatactc ttcctttttc aatattattg aagcatttat cagggttatt      3300
gtctcatgag cggatacata tttgaatgta tttagaaaaa taaacaaata ggggttccgc      3360
gcacatttcc ccgaaaagtg ccacctgacg tctaagaaac cattattatc atgacattaa      3420
cctataaaaa taggcgtatc acgaggccct ttcgtcttca agctgcctcg cgcgtttcgg      3480
tgatgacggt gaaaacctct gacacatgca gctcccggag acgtcacag cttgtctgta       3540 agcggatgcc gggagcagac aagcccgtca gggcgcgtca gcgggtgttg gcgggtgtcg      3600
gggcgcagcc atgacccagt cacgtagcga tagcggagtt ggcttaacta tgcggcatca      3660
gagcagattg tactgagagt gcaccatatc gacgctctcc cttatgcgac tcctgcatta      3720
ggaagcagcc cagtagtagg ttgaggccgt tgagcaccgc cgccgcaagg aatggtgctg      3780
gcttatcgaa attaatcgac tcactatagg gagacccgaa ttcgagctcg ccccgttaca      3840
```

-continued

```
taacttacgg taaatggccc gcctggctga ccgcccaacg accccgccc attgacgtca      3900
ataatgacgt atgttcccat agtaacgcca atagggactt tccattgacg tcaatgggtg      3960
gagtatttac ggtaaactgc ccacttggca gtacatcaag tgtatcatat gccaagtacg      4020
cccctattg acgtcaatga cggtaaatgg cccgcctggc attatgccca gtacatgacc      4080
ttatgggact ttcctacttg gcagtacatc tacgtattag tcatcgctat taccatggtg      4140
atgcggtttt ggcagtacat caatgggcgt ggatagcggt ttgactcacg gggatttcca      4200
agtctccacc ccattgacgt caatgggagt ttgttttggc accaaaatca acgggacttt      4260
ccaaaatgtc gtaacaactc cgccccattg acgcaaatgg gcggtaggcg tgtacggtgg      4320
gaggtctata taagcagagc tcgtttagtg aaccgtcaga tcgcctggag acgccatcca      4380
cgctgttttg acctccatag aagacaccgg gaccgatcca gcctccgcgg gatcttggtg      4440
gcgtgaaact cccgcacctc ttcggccagc gccttgtaga agcgcgtatg gcttcgtggg      4500
gatcccccaa agaatcctta gctcccctg gtagagacga agtccctggc agtttgcttg      4560
gccaagggag gggagcgta atggactttt ataaaagcct gagggagga gctacagtca      4620
aggtttctgc atcttcgccc tcagtggctg ctgcttctca ggcagattcc aagcagcaga      4680
ggattctcct tgatttctcg aaaggctcca caagcaatgt gcagcagcga cagcagcagc      4740
agcagcagca gcagcagcag cagcagcagc agcagcagca gcagcagcca ggcttatcca      4800
aagccgtttc actgtccatg gggctgtata tgggagagac agaaacaaaa gtgatgggga      4860
atgacttggg ctacccacag cagggccaac ttggcctttc ctctggggaa acagactttc      4920
ggcttctgga agaaagcatt gcaaacctca ataggtcgac cagcgttcca gagaaccca      4980
agagttcaac gtctgcaact gggtgtgcta ccccgacaga gaaggagttt cccaaaactc      5040
actcggatgc atcttcagaa cagcaaaatc gaaaagcca gaccggcacc aacggaggca      5100
gtgtgaaatt gtatcccaca gaccaaagca cctttgacct cttgaaggat ttggagtttt      5160
ccgctgggtc cccaagtaaa gacacaaacg agagtccctg gagatcagat ctgttgatag      5220
atgaaaactt gctttctcct ttggcgggag aagatgatcc attccttctc gaagggaaca      5280
cgaatgagga ttgtaagcct cttattttac cggacactaa acctaaaatt aaggatactg      5340
gagatacaat cttatcaagt cccagcagtg tggcactacc ccaagtgaaa acagaaaaag      5400
atgatttcat tgaactttgc accccgggg taattaagca agagaaactg ggcccagttt      5460
attgtcaggc aagcttttct gggacaaata taattggtaa taaatgtct gccatttctg      5520
ttcatggtgt gagtacctct ggaggacaga tgtaccacta tgacatgaat acagcatccc      5580
tttctcagca gcaggatcag aagcctgttt taatgtcat tccaccaatt cctgttggtt      5640
ctgaaaactg gaataggtgc caaggctccg gagaggacag cctgacttcc ttggggggctc      5700
tgaacttccc aggccggtca gtgttttcta atgggtactc aagccctgga atgagaccag      5760
atgtaagctc tcctccatcc agctcgtcag cagccacggg accacctccc aagctctgcc      5820
tggtgtgctc cgatgaagct tcaggatgtc attacgggt gctgacatgt ggaagctgca      5880
aagtattctt taaaagagca gtggaaggac agcacaatta cctttgtgct ggaagaaacg      5940
attgcatcat tgataaaatt cgaaggaaaa actgcccagc atgccgctat cggaaatgtc      6000
ttcaggctgg aatgaacctt gaagctcgaa aaacaaagaa aaaatcaaa gggattcagc      6060
aagccactgc aggagtctca caagacactt cggaaaatcc taacaaaaca atagttcctg      6120
cagcattacc acagctcacc cctaccttgg tgtcactgct ggaggtgatt gaacccg         6177
```

```
<210> SEQ ID NO 2
<211> LENGTH: 42
<212> TYPE: DNA
<213> ORGANISM: Homo sapiens
<220> FEATURE:
<221> NAME/KEY: CDS
<222> LOCATION: (1)..(42)
<223> OTHER INFORMATION: Partial sequence of human progesterone receptor

<400> SEQUENCE: 2 aac ttg cat gat ctt gtc aaa caa ctt cat ctg tac tgc ttg        42
Asn Leu His Asp Leu Val Lys Gln Leu His Leu Tyr Cys Leu
1               5                   10

<210> SEQ ID NO 3
<211> LENGTH: 42
<212> TYPE: DNA
<213> ORGANISM: Artificial sequence
<220> FEATURE:
<221> NAME/KEY: CDS
<222> LOCATION: (1)..(42)
<223> OTHER INFORMATION: Mutant sequence UP-1 having a stop codon
      generated 36 nucleotides downstream of the C-2636 deletion

<400> SEQUENCE: 3 aat tgc atg atc ttg tca aac aac ttc atc tgt act gct tga        42
Asn Cys Met Ile Leu Ser Asn Asn Phe Ile Cys Thr Ala
1               5                   10

<210> SEQ ID NO 4
<211> LENGTH: 14
<212> TYPE: PRT
<213> ORGANISM: Homo sapiens

<400> SEQUENCE: 4

Asn Leu His Asp Leu Val Lys Gln Leu His Leu Tyr Cys Leu
1               5                   10

<210> SEQ ID NO 5
<211> LENGTH: 13
<212> TYPE: PRT
<213> ORGANISM: Artificial sequence
<220> FEATURE:
<223> OTHER INFORMATION: Partial translated sequence of mutant UP-1

<400> SEQUENCE: 5

Asn Cys Met Ile Leu Ser Asn Asn Phe Ile Cys Thr Ala
1               5                   10

<210> SEQ ID NO 6
<211> LENGTH: 42
<212> TYPE: DNA
<213> ORGANISM: Artificial sequence
<220> FEATURE:
<223> OTHER INFORMATION: Synthetic EcoRI-SspI fragment for use to
      generate mutation on the human glucocorticoid receptor ligand
      binding site

<400> SEQUENCE: 6
aattccccga ggcggcagct gaaatcatca ccaatcagat ct        42
```